United States Patent [19]

Kingston, Jr. et al.

[11] Patent Number: 5,126,272
[45] Date of Patent: Jun. 30, 1992

[54] SYSTEM FOR DETECTING TRANSITION AND RARE EARTH ELEMENTS IN A MATRIX

[75] Inventors: Howard M. Kingston, Jr., Gaithersburg, Md.; John M. Riviello, Santa Cruz, Calif.; Archava Siriraks, Rockville, Md.

[73] Assignee: United States of America, Washington, D.C.

[21] Appl. No.: 318,800

[22] Filed: Mar. 2, 1989

[51] Int. Cl.$^5$ .................... G01N 30/14; G01N 33/20
[52] U.S. Cl. ........................................ 436/77; 436/79; 436/80; 436/81; 436/82; 436/84; 436/161; 210/656; 210/672; 210/688; 210/674
[58] Field of Search ................ 436/77, 79, 80, 81, 436/82, 84, 161; 210/656, 672, 688, 674; 73/61.1 C

[56] References Cited

PUBLICATIONS

Strelow, F. W. E. "Quantitative separation of lanthanides and scandium from barium, strontium and other elements by cation-exchange chromatography in nitric acid", Anal. Chim. Acta., Nov. 1, 1980, pp. 249–254.

Liren, Chen et al. "Ion exchange chromatograph with coulometric detector for the determination of ionic substances", Proc. Sino-West Germ. Symp. Chromatography 1983, pp. 506–513.

Kingston, H. M., Barnes, I. L., Brady, T. J., Champ, M. A., and Rains, T. C., "Separation of Eight Transition Elements in Estuarine and Sea Water with Chelating Resin and Their Determination by Graphite Furnace Atomic Absorption Spectrometry," Anal. Chem., 50, 14 (1978).

Kingston, H. M., and Pella, P. A., "Preconcentration of Trace Metals in Environment and Biological Samples by Cation Exchange Filters for C-Ray Spectrometry," Anal. Chem. 53, 2 (1981).

Gunter Knapp, Jurt Muller, Martin Strunz and Wolfard Wegscheider, "Automation in element Pre-concentration with Chelating Ion Exchangers", Journal of Analytical Atomic Spectrometry, vol. 2, (1987).

Greenberg, R. R., and Kingston, H. M., "Simultaneous Determination of Twelve Trace Elements in Estuarine and Sea Water Using Pre-Irradiation Chromatography," J. Radio. Anal. Chem., 71, 147 (1982).

Werefridus W. Van Berkel, Arent W. Overbosch, Gjalt Feenstra and Frans J. M. J. Maessent, "Enrichment of Artificial Sea Water. A Critical Examination of Chelex-100 for Group-wise Analyte Pre-Concentration and Matrix Separation", J. of Ana. Atomic Spectromety, vol. 3, pp. 249–257 (1988).

Ion-Exchange Chromatography (H. F. Walton, Editor, 1976).

Primary Examiner—David L. Lacey
Assistant Examiner—David Redding

[57] ABSTRACT

A method for the detection of trace transition elements and rare earth elements in a sample also containing alkali metals or alkaline earth elements. The sample is flowed through a chelator column which retains the transition elements and rare earth elements. Then a first eluent (e.g. ammonium acetate) is passed through the column to strip the alkali and alkaline earth metals retained on the column. Then a second eluent (e.g. a strong acid) is passed through the chelator column to remove the transition elements in a chelator effluent which flows through an ion exchange resin concentrator to retain only the transition elements and rare earth elements. Then, a chelator complexing agent (e.g. pyridine-2,6 dicarboxylic acid or an oxalate) flows through the concentrator column to remove the transition elements and rare earth elements.

27 Claims, 21 Drawing Sheets

Seawater (HKSW-3) and blank:

| Peaks: | Seawater (ng) | Blank (ng) |
|---|---|---|
| 1. $Fe^{3+}$ | 85.34 (3.4 ng/mL) | 10.20 |
| 2. $Cu^{2+}$ | 44.05 (1.8 ng/mL) | 1.65 |
| 3. $Ni^{2+}$ | 31.50 (1.3 ng/mL) | 1.22 |
| 4. $Zn^{2+}$ | 128.10 (5.1 ng/mL) | 18.50 |
| 5. $Mn^{2+}$ | 45.75 (1.8 ng/mL) | ND |

Sample: 25mL
Detection: 0.05 AUFS

Note: Blank data was taken after 14 runs

Standard:

| Peaks: | ppb | Peaks | ppb |
|---|---|---|---|
| 1. $Fe^{3+}$ | 2.45 | 4. $Zn^{2+}$ | 4.67 |
| 2. $Cu^{2+}$ | 4.67 | 3. $Co^{2+}$ | 4.67 |
| 3. $Ni^{2+}$ | 4.67 | 6. $Mn^{2+}$ | 4.67 |

Sample: 40 g

Detection: 0.2 AUFS

| Peaks: | Chelation IC (ppb) | NAA (ppb) |
|---|---|---|
| 1. $Fe^{3+}$ | 2.20 ± 0.26 (11.8%) | 2.10 ± 0.3 |
| 2. $Cu^{2+}$ | 1.73 ± 0.09 (5.2 %) | 2.01 ± 0.05 |
| 3. $Ni^{2+}$ | 1.32 ± 0.04 (3.0 %) | 1.30 ± 0.2 |
| 4. $Zn^{2+}$ | 5.12 ± 0.21 (4.1 %) | 4.90 ± 0.2 |
| $Co^{2+}$ | NA | 0.044 ± 0.003 |
| 5. $Mn^{2+}$ | 1.83 ± 0.09 )4.9 %) | 1.89 ± 0.03 |

Sample: 40.2 g (% RSD - Peak Area), N=12

| Peaks: | Chelation IC (ug/g) | Certified Values (ug/g) |
| --- | --- | --- |
| 1. $Fe^{3+}$ | 210.21 ± 4.2 | 195 ± 34 |
| 2. $Cu^{2+}$ | 65.0 ± 0.82 | 64 ± 3.5 |
| 3. $Ni^{2+}$ | NA | 1.03 ± 0.19 |
| 4. $Zn^{2+}$ | 863.40 ± 5.5 | 863 ± 14 |

Sample contains 0.15% Ca and 0.128% Mg

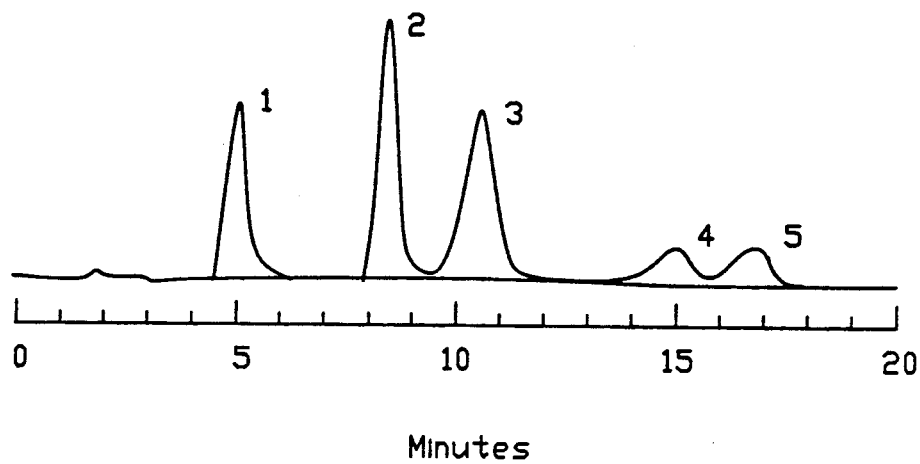
| Peaks: | Chelation IC (ug/g) | Certifed Values (ug/g) |
|---|---|---|
| 1. $Fe^{3+}$+ | NA | |
| 2. $Cu^{2+}$ | 162 ± 3.5 | 158 ± 7 |
| 3. $Zn^{2+}$ | 110 ± 5.3 | 1234 ± 8 |
| 4. $Mn^{2+}$ | 9.8 ± 0.02 | 9.9 ± 0.8 |
| 5. $Fe^{2+}$ | NA | |
Sample contains 120 ± 7 ug/g Ca and 9.9 ± 0.8 ug/g Mg
FIG.—21

SYSTEM FOR DETECTING TRANSITION AND RARE EARTH ELEMENTS IN A MATRIX

BACKGROUND OF THE INVENTION

In many environmental and biological samples, the matrix contains large amounts of alkali and alkaline earth metals as compared to the transition elements and rare earth elements. This concentration difference can be 1,000 to 1,000,000 times greater than the transition elements and rare earth elements of interest. Conventional ion exchange concentration methods for determination of trace and ultra-trace level of transition elements and rare earth elements cannot be used since these methods are typically not selective enough for the specific ions.

Iminodiacetate chelating resin has been used for brine type matrixes and offers a number of advantages. In such procedures, the alkali and alkaline earth metals are separated as a class from the transition elements and rare earth elements. Further, the transition elements and rare earth elements can be readily eluted using mineral acids, which is an acceptable matrix for some analytical techniques. However, the transition elements and rare earth elements may be present at insufficient concentrations to be effectively analyzed. Furthermore, no effective means have been provided of coupling the class separation with a technique for chromatographic separation of the individual transition elements and rare earth elements. In that regard, there are considerable difficulties in such coupling for samples in which the trace metals are present and the concentration too low for chromatography or other methods. Further, direct coupling could not be performed because of the vast differences in the eluants used for removing the transition elements and rare earth elements from the chelator columns and those employed for chromatography.

An established technique for separating transition and rare earth elements as a class from alkali and alkaline earth metals is open column chromatography. It uses a variety of tubes packed with resin with only gravity and atmospheric pressure to force a liquid phase through the resin column. Open column chromatography is most often a preparatory technique to perform a separation where a portion of the effluent is collected in a batch mode to be analyzed later by another method.

This particular open column chromatography uses a specific class of chromatographic fixed-phase resin. (A commercially available analytical grade chelating resin is Chelex-100 currently manufactured by Bio-Rad, the resin was first produced in the mid 1960's by Dow under the name Dow A-1). This chelating resin differed from ion exchange resins by using chelating mechanisms to hold elemental ions. The effectiveness as a chelator is pH-dependent and has a wide range of selectivities ($10^{11}$). The active group in the resin is iminodiacetate. The resin was first used in the late 1960's for the collection of transition elements from high salt matrixes such as sea water, but no separation of elements was performed on the resin. Those elements that did not chelate were retained on unused sites on the resin, but some were lost from the column when less resin capacity was used than necessary to concentrate all ions from a sample. The resin was used as a collector of transition elements in solutions high in alkali and alkaline earth elements with residual alkali and alkaline earth elements remaining on residual resin capacity. At that time it was stated that no complete separations of specific elements or ions would be possible using this type of chelating resin.

Riley and Taylor published several papers collecting the trace transition elements in sea water, allowing some of the alkali and alkaline earth elements (most notably: Na, K, Ca, Nd Mg, etc.) to flow through a small column and elute all the ions with mineral acids or base. The elemtns were concentrated and the alkali and alkaline earth elements were reduced sufficiently to aid in the detection of the transition elements by atomic absorption spectroscopy.

A separation was developed in 1978 using this resin that did separate the alkali and alkaline earth elements completely from the retained transition and rare earth elements (1, 2, 3, 4). Reference 2 contains a review of the previous work to that point, as well as a description of this new separation method that used the resin to completely separate classes of elements. This work was demonstrated using open column chromatography on sea water prior to analysis by either graphite furnace atomic absorption, x-ray fluorescence or neutron activation analysis. Sea water is of interest as a very difficult matrix but more importantly, it is the most difficult of many real analytical samples. It contains very high concentrations of alkali and alkaline earth elements that are many times greater than the trace transition and rare earth elements which are of primary interest, $10^8$ and $10^6$ greater, respectively. Almost all naturally occurring samples have this same type imbalance; high concentrations of alkali and alkaline earth elements compared to the trace transition and rare earth elements. Since it is the alkali and alkaline earth elements that interfere with most analytical chemical instrumental analyses, the ability to preconcentrate the trace transition elements and to totally remove the alkali and alkaline earth elements prior to analysis is a powerful tool for analytical chemistry.

Due to its wide applicability, this procedure has been applied to many acid-digested samples prior to instrumental analysis since 1978. It has been applied as a sample preparation method for the analysis of trace elements in biological, botanical, brines, sea water, fresh water, and other samples (5-11). It was further modified using a new method to directly introduce the resin containing the trace elements after elimination of the alkali and alkaline earth elements into a nuclear reactor to perform neutron activation analysis (6, 8, 10) and other instrumental methods. Several of these applications required modification of the final sample form for compatibility with a particular instrument but most of the basic method for the separation remained unchanged from the original 1978 (4) papers to present.

The concentration of the transition and rare earth ions and subsequent separation of alkali and alkaline earth ions are difficult to control because they are dependent on many parameters. Experienced chromatographers are often unable to use it in a routine manner because of these difficulties. Several examples identify and documented the challenge of controlling the method of this particular open column chelation chromatography. After reviewing literature, four chromatographers could not obtain the optimal efficient recoveries reported for several elements (12). Another group tried to control the trace element preconcentration without the separation by using flow injection and complained of the difficulty of controlling the resin that shrinks and swells in different ion complexed forms and at different pHs necessary to perform the concentration (13). They then analyzed the sample by inductively coupled plasma spectrometry after batch collection. They were unsuccessful in demonstrating quantitative recoveries for many of the trace elements and were not able to identify conditions that would provide quantitative results for the elements tested. All of these papers mentioned used Chelex-100 resin.

One problem with the open column system is that all of the parameters cannot be totally controlled because of the physical constraints of the system. A recent paper describing the inability to achieve complete retention indicates how difficult it is to control this type of reaction under open column conditions, even for experienced chromatographers (12). It is very easy to lose control of the chemistry, or change one parameter that will affect the retention or elution mechanism and cause an error.

The flow rate cannot be controlled in the open column system. To increase the flow rate researchers used larger particle sizes than are recommended in the original paper. This is one common problem introduced by chromatographers when attempting to duplicate the conditions of the original method. If the same particle size resin were used in open column than is necessary for the pressurized system, the flow rate would decrease dramatically and the separation time would increase to approximately eight to ten hours per open column.

The resin that is used in the prior open column methods (Chelex-100) is soft and could be crushed by pressure if used in pressurized columns with dimensions necessary to achieve optimum capacity and at optimum flow rates. Chelex-100 has properties similar to a gel and is not cross-linked sufficiently to permit the resin to function in the pressurized system. It shrinks and swells 50-100% in volume during pH and chelated ion changed.

The open column method does not permit the system to be used directly on-line with an instrument for detection. It is confined to batch mode and prevents the direct coupling of the column to an instrument, to a second column, or to a detector. It also does not permit the addition of the sampl in acid form. This is a new and important procedure for some samples due to the hydrolysis of iron and aluminum, and other elements at the pH range where the resin changes from being a weak ion exchanger to a very powerful chelator (approximately pH 5., (1, 2, 3, 4, 5). This is important to the usefulness of the system for certain types of samples such as biological, botanical, sediment and geological samples that contain large quantities of these elements.

SUMMARY OF THE INVENTION

In accordance with the present invention a system has been provided for the detection of the transition elements and/or rare earth elements in an aqueous sample which also contains high concentrations of alkali and alkaline earth metals. The system is particularly effective for determination of the transition elements and/or rare earth elements in sea water, industrial waste streams, biological fluids and biological tissue samples (e.g. oyster tissue or bovine liver).

A major advantage of the invention is that it permits isolation and concentration of the transition elements and/or rare earth elements as a class, followed by chromatographic separation in a continuous process. A preferred embodiment of the present invention is as follows. (For simplicity of description, the detection of transition elements will be described. However, the invention encompasses the detection of rare earth elements and lanthanides as well.)

In step one, the transition elements, and, in some instances, some portion of alkali and alkaline earth metals are retained on a chelator column, (e.g. of the iminodiacetate chelating resin type). If the system is to be used on line in combination with HPLC, the resin preferably is in macroporous form to withstand the pressures employed in various downstream portions of a closed system. Also, highly cross-linked microporous resins may be used. Further, gels of similar function can be used. If the system is not on line, other forms of the resin, e.g. microporous, may be used.

In step two, a first eluant (e.g. ammonium acetate) is passed through the column to strip alkali and alkaline earth metals, if retained on the column, in a waste stream without disturbing the transition elements and rare earth elements.

(In an alternative embodiment, the second step may be eliminated if the chelating resin is sufficiently specific to retain the transition or rare earth elements but not the alkalai and alkaline earth metals in the first step.)

In step three, after class separation, a second eluant (e.g. a strong acid) is passed through the chelator column to remove the transition elements in a chelator effluent.

In step four, the chelator effluent is directed to a concentrator column (in the form of an ion exchange resin) where the transition elements are retained. The remainder of the chelator effluent flows to waste. In one embodiment, the concentrator column is in cationic form.

In step five, the cation resin in the concentrator column is in hydronium ion form after passage of the strong acid second eluant. It is equilibrated to another cationic form. The preferred cation is ammonium as it does not interfere with subsequent chromatographic analysis. Cation equilibration permits effective elution of the transition elements and rare earth elements from the concentrator column in the next step.

In step six, a third eluant, a chelation complexing agent, preferably PDCA (pyridine-2,6 dicarboxylic acid) or an oxalate flows through the concentrator column to remove the transition elements and rare earth elements from the column in a concentrator effluent.

In optional but preferred step seven, the transition elements and rare earth elements from the concentrator column are analytically separated as on a chromatographic column, preferably using the eluant of step six.

In step eight, the effluent from the chromatographic column is directed to a detector for detection. In one embodiment, the transition elements and rare earth elements are reacted with a post-column reagent (e.g. PAR) and detected by a UV-VIS detector.

In an alternative embodiment, selected transition elements (e.g. iron) in the sample are removed in the concentrator means stage from the stream being analyzed by the detector. This may be accomplished by (a) retaining the selected transition element so firmly that it is not eluted from the concentrator column in the concentrator effluent, (b) retaining the selected transition element so weakly that it passes early through the detector, or (c) not retaining such selected transition element on the concentrator means when the chelator effluent passes through it.

In another embodiment, for certain applications, both the concentrator means and chromatographic column may be eliminated. There, the system is under pressurized non-gravity flow. The effluent stream from the chelator column flows in a pressurized, continuou stream directly from the chelator means to the detector. Preferably, the detector is an elemental detector, i.e. one in which the transition and rare earth elements are detected individually, rather than as a class.

The present invention also includes apparatus particularly dapted to perform the method of the present invention. In a preferred embodiment, the apparatus includes chelator means and concentrator means, together with means for supplying the sample to the chelator means. In addition, it includes means for supplying a first eluant and, if necessary, a second eluant to the chelator column and another eluant to the concentrator column. Appropriate valving is provided for sequentially interconnecting the sample and eluant supply means in a predetermined sequence. Suitable valving is also provided to flow an equilibrating agent, specifically a cationic salt, to said concentrator column for equilibrating the same prior to removal of the transition elements by the third eluant.

BRIEF DESCRIPTION OF THE DRAWINGS

FIGS. 16-21 illustrate the analysis of various samples using of the present invention.

DETAILED DESCRIPTION OF THE PREFERRED EMBODIMENTS

The invention is applicable to any aqueous liquid sample which includes transition elements and rare earth elements in a mixture with alkali metals or alkaline earth metals. It is particularly effective for detecting transition elements and rare earth elements which are present at very low concentration in comparison to the alkali and alkaline earth metals. Suitable samples include liquid sea water, industrial waste streams such as plant effluent, acid digested biological materials such as blood, urine, oyster, liver, botanical tissue and the like, and geological samples. For purposes of the present description, unless otherwise stated, the aqueous liquid sample of the present invention will be assumed to be sea water which includes transition elements and rare earth elements at relatively low concentration and which further includes high concentration of alkali metals and alkaline earth metals.

As used herein, transition elements include Pb, Cu, Fe, Ni, Zn, Co, Cd, Mn, Al, Mo, Tl, Sc, W, Ce, Bi, In and V; rare earth elements includes Ce, Y, and Eu; alkaline earth metals include Be, Ca, Mg, Sr, Ba, and Ra.

Figure 1:
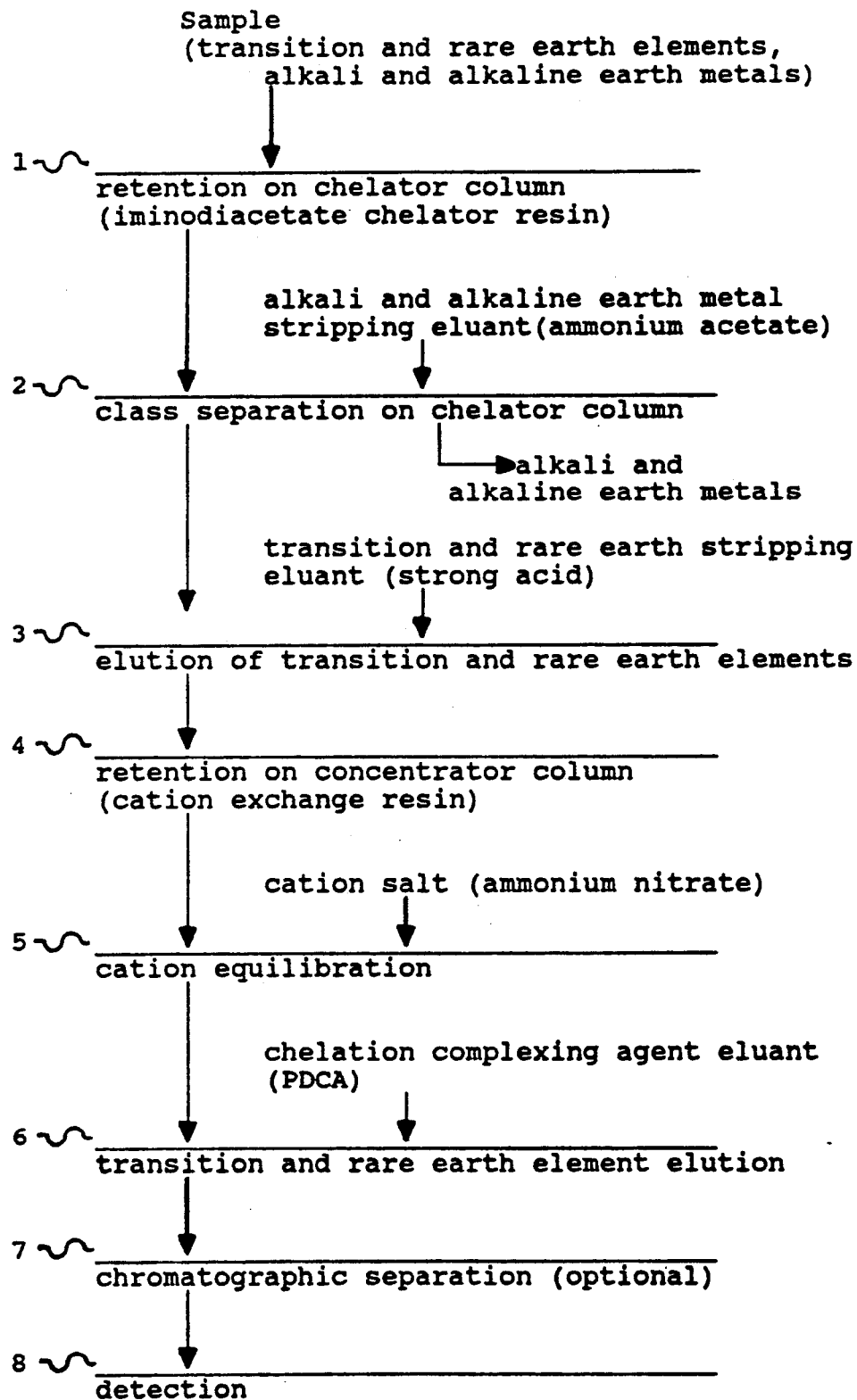
FIG. 1 is a schematic flow diagram of one embodiment of the present invention.

The present invention will be described first by reference to the schematic flow diagram of FIG. 1 which constitutes one preferred embodiment.

In Step 1, the liquid sample is passed through chelator means in the form of a column of chelating resin of a type which retains the transition elements and rare earth elements, and, probably, portions of alkali and alkaline earth metals but which passes the remainder of the sea water, including anions such as chloride, fluoride, phosphates, and most hydrocarbons.

Microporous iminodiacetate chelating resins have been used effectively in the past for the retention of Step 1. One such resin is sold under the trademark Chelex-100 by Bio-Rad. While such resin may be used for purposes of the present invention for low pressure applications, it is not suitable for high pressure applications because it is too soft and may be crushed by high pressures useful in such pressurized system. For this reasons, it may preferable to use a macroporous iminodiacetate resin such as Duolite E5466 sold by Rohm & Haas, further ground to the desired sizing (e.g. $-400$ mesh). Such resins differ from the Chelex-100 primarily in the degree of cross-linking and porosity. For example, such macroporous resins typically have on the order of 10-20% to as high as 60% cross-linking in comparison to Chelex-100 which may have on the order of 2-4% cross-linking.

The iminodiacetate resins typically include such functional groups bound to resin substrates comprising styrene-divinylbenzene copolymers. Suitable resin bead sizes for the chelating resin are in the order of 10 to 100 microns.

Iminodiacetate is one of the preferred functional groups for the chelating resin because of its long use for transition elements and rare earth elements, its consequence known effective properties and because its availability. However, other functional groups may be used so long as they function generally in the same manner, i.e. by partially or completely separating transition elements and rare earth elements from alkali metals and alkaline earth metals from a liquid sample or have a high selectivity for specific group of transition or unique group of elements. Suitable functional groups include thiols, amino acid chelators, carboxylates, polyamines and more specifically, 8-hydroxyquinoline, dithiocarbonate, amidoxime, and aminomethyl phosphonic acid.

Typically, the chelator column has vastly higher capacity than the chromatographic column (e.g. 100 to 1000 times as high). Suitable capacity for the chelator column is about 0.1 to 2 meq/ml of resin compared to 30-300 meq/ml of resin in the chelator. The change of reagents required for this transition is accomplished using the concentrator column.

It is preferable to buffer the chelator column with a buffering agent (e.g. ammonium acetate) which is effective in this pH range. Other buffers such as lithium, sodium, or potassium acetate may also be used as a buffer and eluant during this stage of chelation. However, such alkali metal ions can interfere with metal detection by instruments, especially of the flame spettrometry type. The acetate ion participates in the mechanism that removes the alkaline earth metals calcium and magnesium. It stabilizes the free calcium and magnesium in solution and should be present for efficient separation using the iminodiacetate resin.

For the above reasons, the chelator column is pre-buffered with ammonium acetate, suitably at a concentration of 1-2 molar and a flow rate of 1-3 ml/min.

The conditions during Step 1 are such that the pH is between about 5 and 6 and that the transition elements and rare earth elements do not consume the entire column capacity. Some transition elements and rare earth elements may be complexed to a higher pH than 6. However, the general condition between 5 and 6 is preferable. Excess capacity of 5 to 10 time the level of transition elements is suitable for quantitative retention. Such capacity is calculated on the basis of the transition metal, rather than the alkali or alkaline earth metals.

The elements are retained on the resin in excess capacity until the capacity has been consumed. At this point the resin has been converted to an alkali and alkaline earth form.

There is an alternative procedure to avoid hydrolysis of some transition elements and rare earth elements which can occur at a pH above 3.5. Oxidation and hydrolysis can cause transition metal loss with consequent non-quantitative recovery of metal ions due to un-retained metals of molecular instead of free metal ions or adsorption of metal ions by tubing or plastic sample container and decreases kinetics of the iminodiacetate and metal ions. The reaction may proceed during long term storage while the samples are in an auto sampler or the like. One solution to this possible problem is to maintain the sample at a low pH (e.g. below 2-3), to avoid oxidation or hydrolysis of metal ions. So, because the chelating resin becomes effective at pH 5.0-5.5, this acidic sample should be buffered or neutralized (e.g. with 2 molar ammonium acetate), before the sample stream reaches the chelator column.

In Step 2, there is a class separation on the chelator column whereby the alkali metals and alkaline earth metals are stripped from the column leaving the transition elements and rare earth elements on the column. This is accomplished by flowing a first eluant through the column, preferably comprising an acetate anion salt, suitably 2 M ammonium acetate solution. In this stage, the alkali metal ions are retained by an ion exchange mechanism. However, the alkaline earth metal ions, transition and rare earth metals are retained by a chelation mechanism. The removal of the alkali metals is the result of an ion exchange process in which ammonium ions replace the alkali metal ions on the iminodiocetate. Elution of alkaline earth metals (calcium, magnesium, etc.) is the result of ion exchange and chelation.

In Step 3, a second eluant in the form of a strong acid, preferably a mineral acid such as nitric acid, hydrochloric acid, perchloric acid or sulfuric acid, can be used as the eluant to strip the transition elements from the resin. This is because the chelation ability of the resin is pH dependent. Suitable pH levels of acid for elution are $\leq 1$.

A suitable concentration of acid is from 0.5 to 2.5 M. Complete elution of transition elements requires a relatively high concentration of acid (e.g. greater than 0.5 M).

The use of the concentrator column as a transition between the chelator and the analytical column enables the use of higher concentrations of acid than could have been used if the transition elements and rare earth elements were flowed directly from the chelator column to the analytical column.

In Step 4, after the transition elements and rare earth elements are eluted from the chelator column, they are passed in the strong acid eluant to the concentrator column on which they are retained. The concentrator column comprises a high capacity cation exchange resin suitably including sulfonate ion exchange sites. The preferred capacity is on the order of 2 meq/ml or higher. The trace metals are retained by the sulfonated sites in an ion exchange process. Functionally, the concentrator column serves a a "interface" for the concentration-matrix elimination on the chelator column and the subsequent separation of the transition elements and rare earth elements on an analytical column, preferably of the chromatographic column. The concentrator column suitably has a capacity of about 0.1 to about 1 meq/column, and preferably, about 0.4 to about 0.6 meq/column. The concentrator column is used to collect the transition elements and rare earth elements in acid medium. (After Step 4, the resin in the concentrator column is in hydronium ion form.)

In Step 5, the resin in the concentrator column is converted from the hydronium ion form to another cation form by equilibrating the column with a cationic salt. This permits the transition elements and rare earth elements to be removed by an appropriate chelation complexing agent such as PDCA. If there were no equilibration, large amounts of the hydronium ion from the concentrator resin would interfere with effective elution of the transition metal with the complexing agent. Since PDCA is an amino acid, the hydronium ion causes protonation of the weak acid which disrupts its ionization equilibrium. This can cause separation problems. When the concentrator resin is converted from the hydronium ion form to the ammonium ion form, the PDCA eluant can readily elute the transition elements and rare earth elements from the concentrator column.

An effective cation equilibrator is ammonium nitrate which elutes the hydronium ion but due to the relatively dilute eluant, from 0.05 to 0.1 molar and preferably around 0.1 molar, the transition elements and rare earth elements are not eluted. A required pH level for the ammonium nitrate is on the acidic side (e.g. pH 3-4), in order to prevent hydrolysis of the transition metal ions which would lower their affinity for the concentrator resin. While salts of alkali metals may be used to convert the concentrator resin from the hydrogen ion to the corresponding cation form, these elements may cause problems with specific methods of detection. Although ammonium nitrate is preferred, ammonium salts with other anions such as chloride and sulfate may also be employed.

In Step 6, the transition elements and rare earth elements are eluted from the concentrator column by the addition of a chelation complexing agent. In this step, the transition metal ions complex with the complexing agent to form an anionic complex which does not react with the ionic sites on the cation echange resin. Suitable pH levels for the complexing agent are from about 4.0 to about 4.8. Suitable concentration of such complexing agent is from about 5 to about 50 mM. While PDCA is preferred, other chelating agents which form strong anionic complexes with transition elements may also be used. Such eluants include as oxalic acid, tartaric acid and citric acid.

In Step 7, the transition elements and rare earth elements eluted in the PDCA are supplied to an analytical system, preferably a chromatographic column. Suitable conditions for chromatography are as follows. A suitable flow rate for a separator column, of the HPIC-CS5 type supplied by Dionex Corporation, is at the rate of 1 ml/min. Other chromatographic columns suitable for metal separation may also be used.

After separation, the effluent from the column may be mixed with a post column reagent prior to detection. A suitable post column reagent is 0.2 mMPAR (4-(2-pyridylazo)resorcinol) mixed with 1 M acetic acid and 3 M ammonium acetate.

Referring to Step 8, the transition and rare earth elements are detected, preferably using post column reaction. The PAR reagent is a suitable complexing agent that readily forms a complex with the transition elements and rare earth elements. The resulting metal-PAR complex is detected by measuring at 520-540 nm.

Overall, any number of detectors may be used including x-ray fluorescence, atomic adsorption, inductively coupled plasma spectroscopy(ICP),ICP-mass spectrometry graphic furnace atomic adsorption, isotope dilution mass spectrometry and neutron activation analysis.

If desired for certain specialty applications, the system including Steps 1-6 may be employed without chromatographic separation so that the transition elements and rare earth elements separated from Step 6 may be directed to a detector without chromatographic separation.

In certain circumstances, the second step in the procedure may be eliminated so long as the chelating resin in the chelating column is sufficiently specific to retain the transition or rare earth elements but not the alkali or alkaline earth metals. In such instances, there is no need to strip or wash the alkali and alkaline earth metals with ammonium acetate as described above.

One specific form of chelating resin which has been found to have the desired degree of specificity is an 8-hydroxyquinoline chelator (sold under the designation XE-305, 8-hydroxyquinoline bonded resin by Seastar Instruments). Suitably the column in equilibrated as with ammonium chloride at a pH of 10. Buffered sea water at pH of 7 can be passed through the column which concentrates the transition elements but does not retain the alkali and alkaline earth metals. Thereafter, the transition elements are eluted with the same eluant as set forth above and the remainder of the procedure is as described.

In the procedure described above, all of the transition and rare earth elements in the sample are analyzed. However, the system can also be used in a mode in which selected transition elements (e.g. iron) of the sample are removed in the concentrator means stage from the stream being analyzed in the detector. One reason for doing so would be if the particular transition element is present at such a high concentration that it would mask or interfere with detection of the remainder of the transition elements.

This alternative procedure may be accomplished by (a) retaining the selected transition element so firmly that it is not eluted from the concentrator column in the concentrator effluent, (b) retaining the selected transition element so weakly that it passes through the detector early or, (c) not retaining such selected transition element on the concentrator column when the chelator effluent passes through it.

Referring to procedure (a), one technique is to use a concentrator column and eluant for the chelator column under conditions that elute the transition elements other than the selected one from the concentrator column. For a system which eliminates iron from detection, after the alkali and alkaline earth metals have been eluted from the chelator column in step 2, an oxalic acid/ammonium hydroxide eluant may be used to elute all transition elements including iron from the chelating column to the concentrator column. In this instance, the concentrator is suitably an anion exchange resin (e.g. functionalized by a quaternary ammonium salt). Thereafter, the same chelation complexing agent (PDCA) will elute all transition elements other than iron. The anion exchange resin would not be used when subsequent chromatography is employed.

Referring to technique (b), the cation exchange column described above is used with an oxalate eluant. Here the concentrated iron from the chelator column elutes in the first 2 ml of the oxalate eluant while the other transition elements have an elution volume of 5-10 ml.

Figure 13:
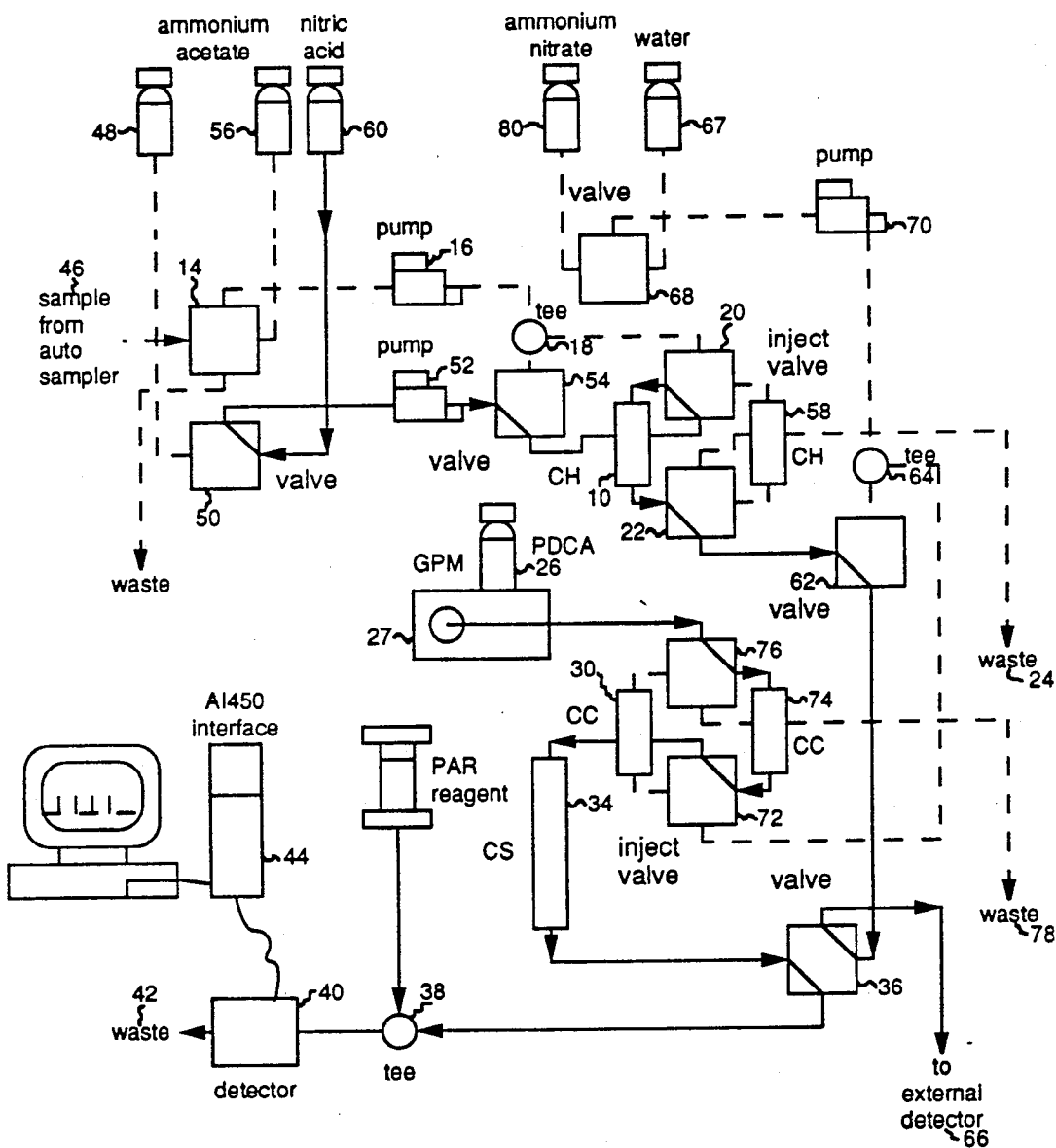

For the analysis of certain samples, separation of the individual elements on a chromatographic column are not required. Accordingly, an alternate system is to pass the chelator effluent stream directly to a detector which is capable of detecting individual transition or rare earth elements in a stream without prior separation. For this type of system, the concentrator column may be eliminated because the same eluant used to strip the transition elements from the chelator column can pass directly to the detector. Suitable elemental detectors include laser enhanced ionization (LEI), ICP, or ICP, MS. This type of system can be used where the chelator column is capable of separating the transition elements from the alkali and alkali earth metals without a wash or where a wash is necessary. An example of the latter approach is shown in the valve setting of FIG. 13 as described in Example 1. Any of the chelator resins previously described may be used in this embodiment (e.g. iminodiacetate and 8-hydroxyquinoline). Suitable conditions are as illustrated in FIG. 13.

The following examples serve to illustrate the use of the method and apparatus of the present invention.

EXAMPLE 1

This example specifies the conditions and sequence useful for a wide variety of samples. Referring to FIGS. 2-15, the operation of the method of FIG. 1 is illustrated in 14 stages and valve settings for an automated system using two chelator columns, two concentrator columns and a single chromatographic column and detector. Each figure corresponds to a valve setting for suitable consecutive stages in the programming sequence. By appropriate sequencing, while one sample is flowing through one circuit, another sample is flowing through another circuit to maximize the use of the analytical column and detector. However, it should be understood that the system may also be employed by eliminating one of the circuits of chelator column and concentrator column with a corresponding modification of the valving.

Figure 2:
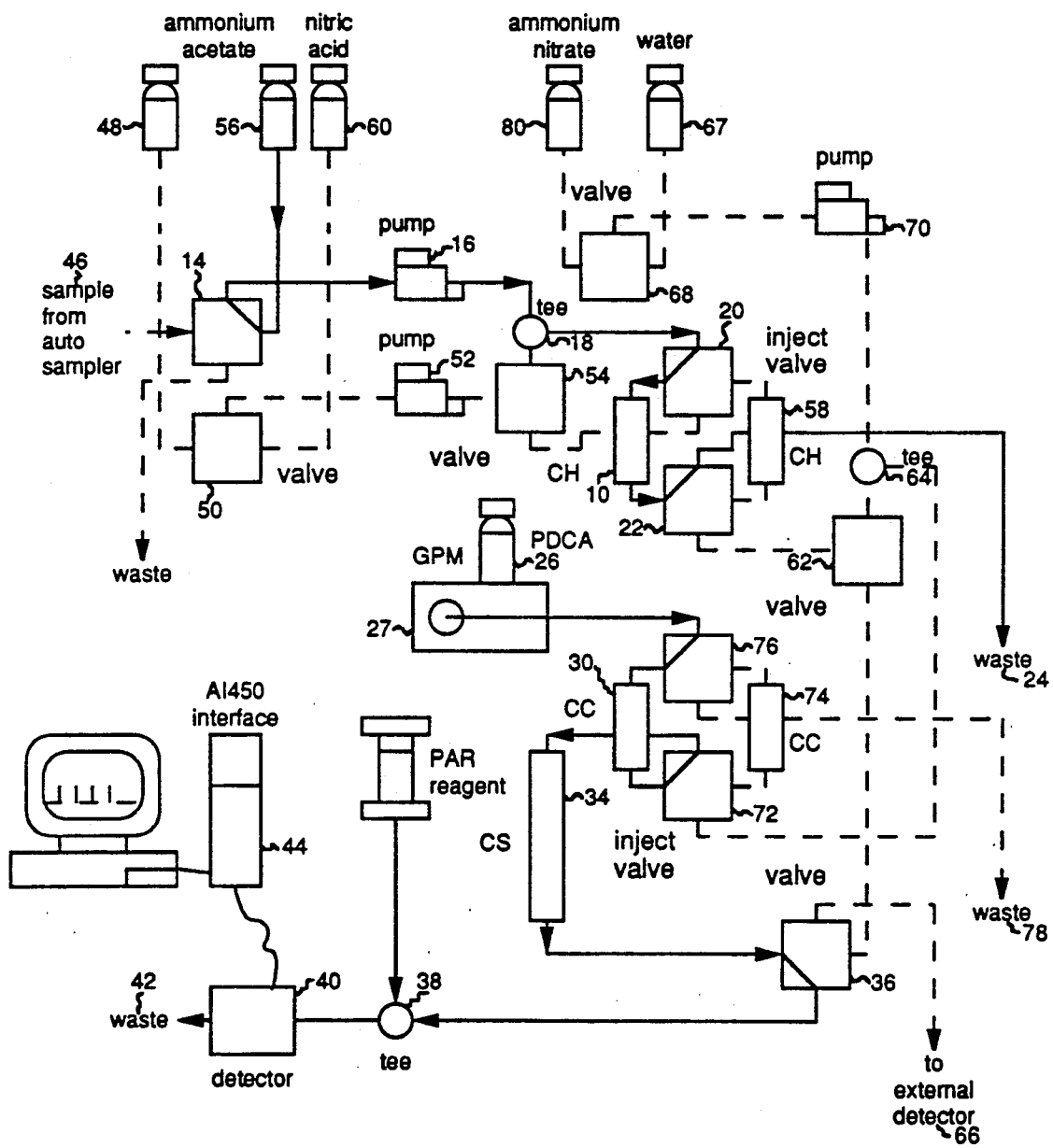
FIGS. 2-15 are schematic representations of apparatus for performing the present invention illustrating two pairs of chelator and concentrator columns with a single chromatographic column and detector.

Referring specifically to FIG. 2, chelator column 10 is first buffered with a suitable buffer, 2 M ammonium acetate (pH 5.5), supplied from pressurized container 56 through valve 14, pump 16, mixing tee 18, valve 20 and passes through chelator column 10 out valve 22 and to waste 24. At the same time, the chelating complexing agent which removes the transition elements form the concentrator column is used to equilibrate the chromatographic column. Specifically, such equilibrating agent (6 mM PDCA) is supplied from pressurized container 26 through pump 27 at 1 ml/min and passes through valve 28 concentrator column 30, valve 32 into analytical column 34 through valve 36 to mixing tee 38, detector 40 and to waste at 42. If transition elements had been concentrated on concentrator column 30, analysis from concentrator column 30 begins at this time. Detector 40 is connected to appropriate recording means 44.

Figure 3:
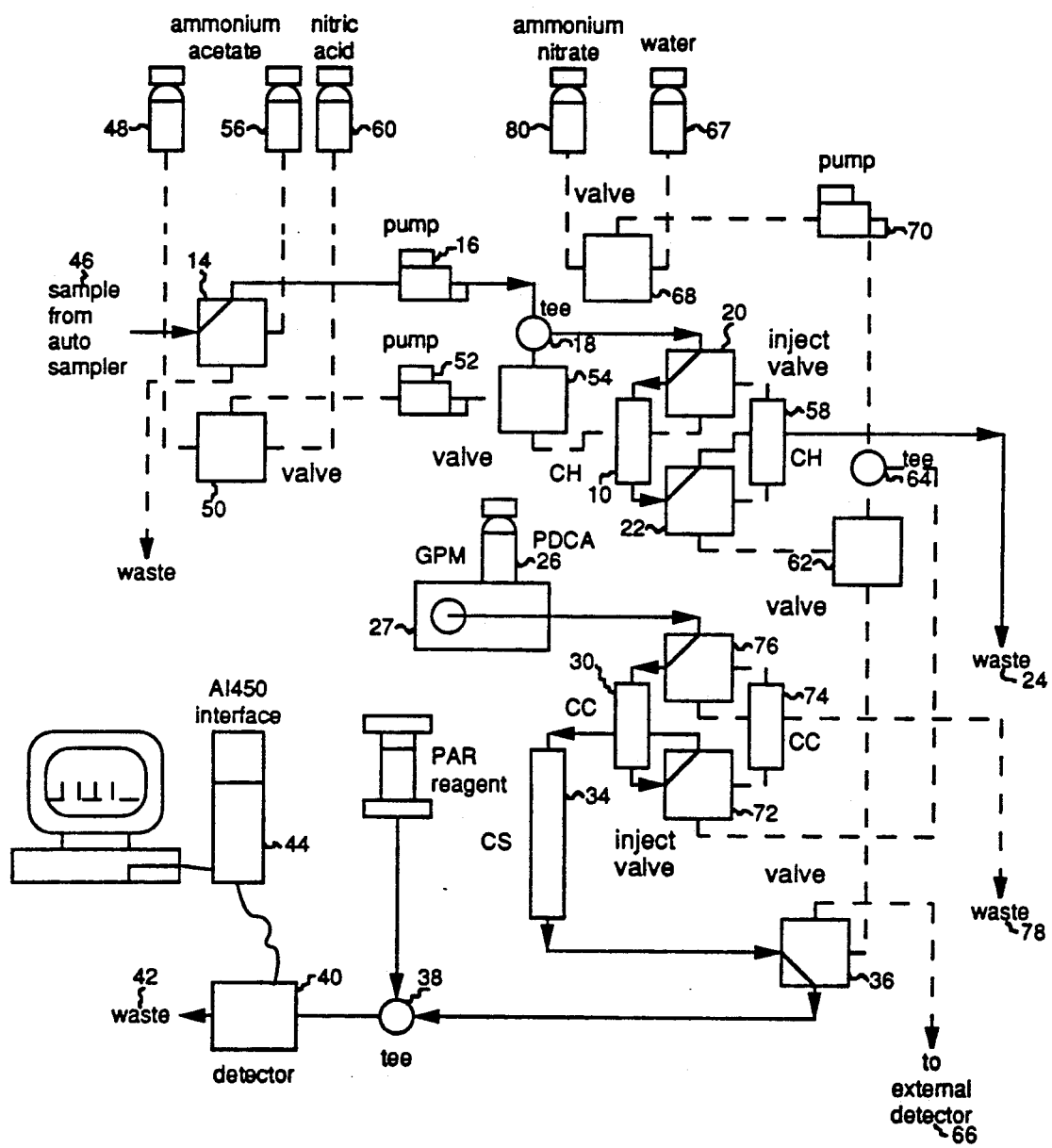

Referring to FIG. 3, sample at a flow rate of 2 ml/min and a pH of 5.2-5.5 from an autosampler (not shown) generally designated by the number 46 is loaded onto chelator column 10 by passing through valve 14, pump 16 (at a setting of 2 ml/min), through mixing tee 18, valve 20, chelator column 10, valve 22 into waste at 24. During this time, analysis of the transition elements, if present from the previous stage, continues.

Figure 4:
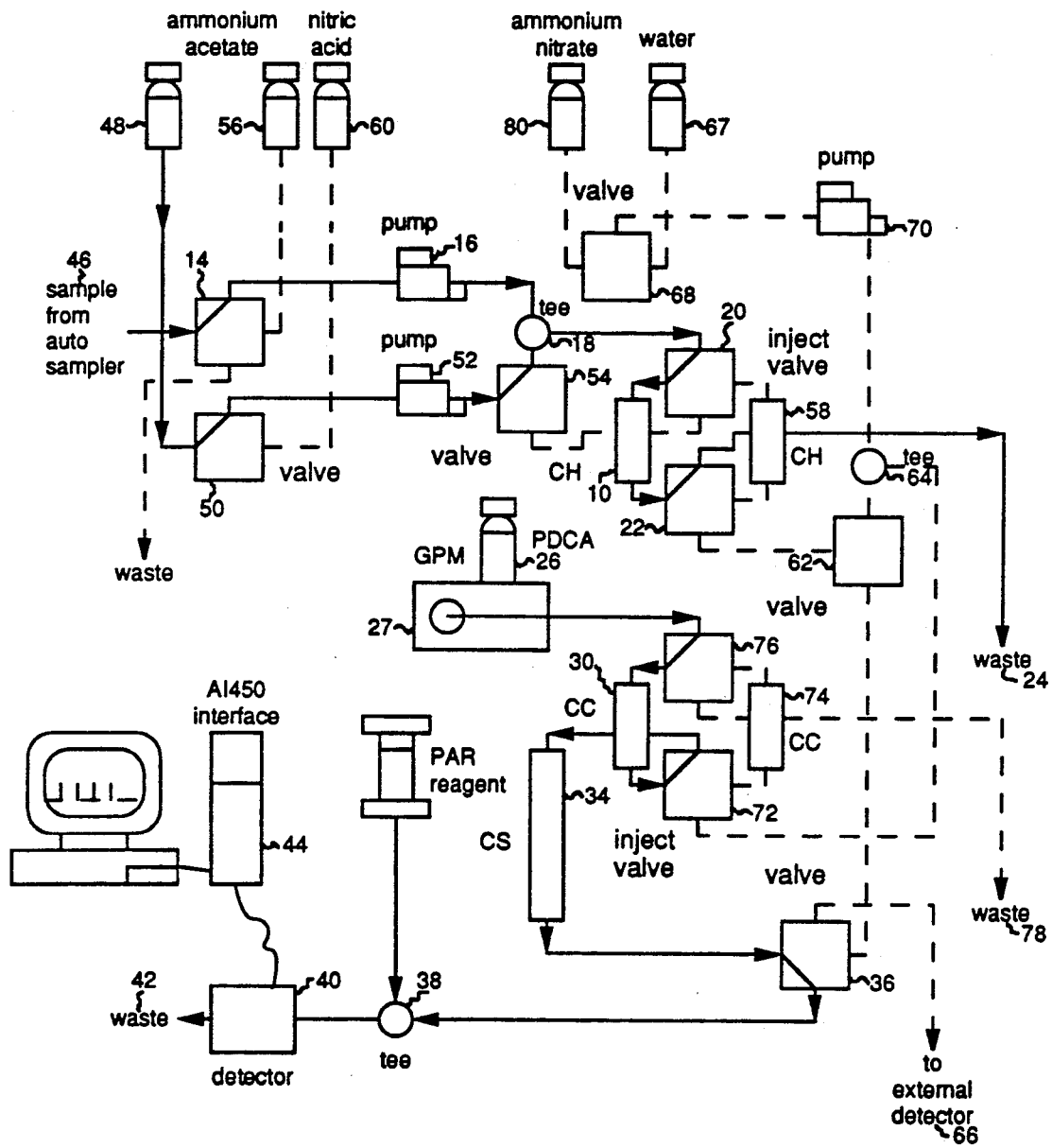

Referring to FIG. 4, an alternate loading procedure is illustrated to avoid metal hydrolysis at pH 5.5. Acidified sample (at pH 2-3) may be used. However, it is neutralized with 2 M ammonium acetate before the sample stream reaches chelator column 10. Here ammonium acetate from pressurized container 48 passes through valve 50, pump 52 (at a setting of 1 ml/min) and valve 54 to mixing tee 18 in which it with sample from source 46 of valve 14 pump 16. Otherwise, the alternative system in FIG. 4 is the same as illustrated in FIG. 2, 3 and 5-15.

Figure 5:
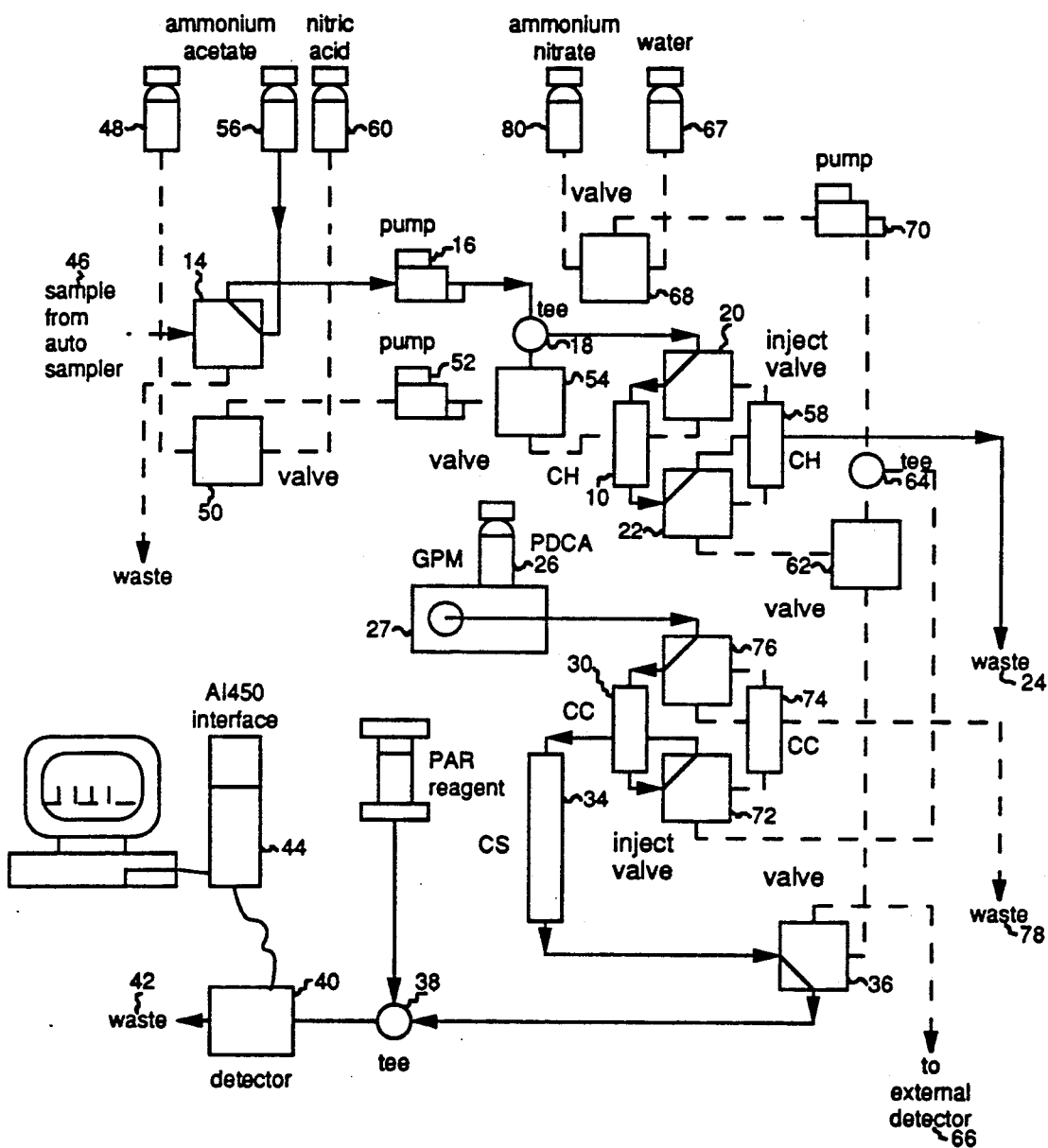

Referring to FIG. 5, alkali and alkaline earth metals are removed from chelator column 10 by passing 2 M ammonium acetate through the chelator. Specifically, ammonium acetate from the source, pressurized container 56, passes through valve 14 pump 16 (set at 2 ml/min) mixing tee 18, valve 20, chelator column 10, valve 22 and to waste at 24. During this stage, analysis of transition elements being removed from concentrator column 30 through analytical column 34 is being detected by detector 40.

Figure 6:
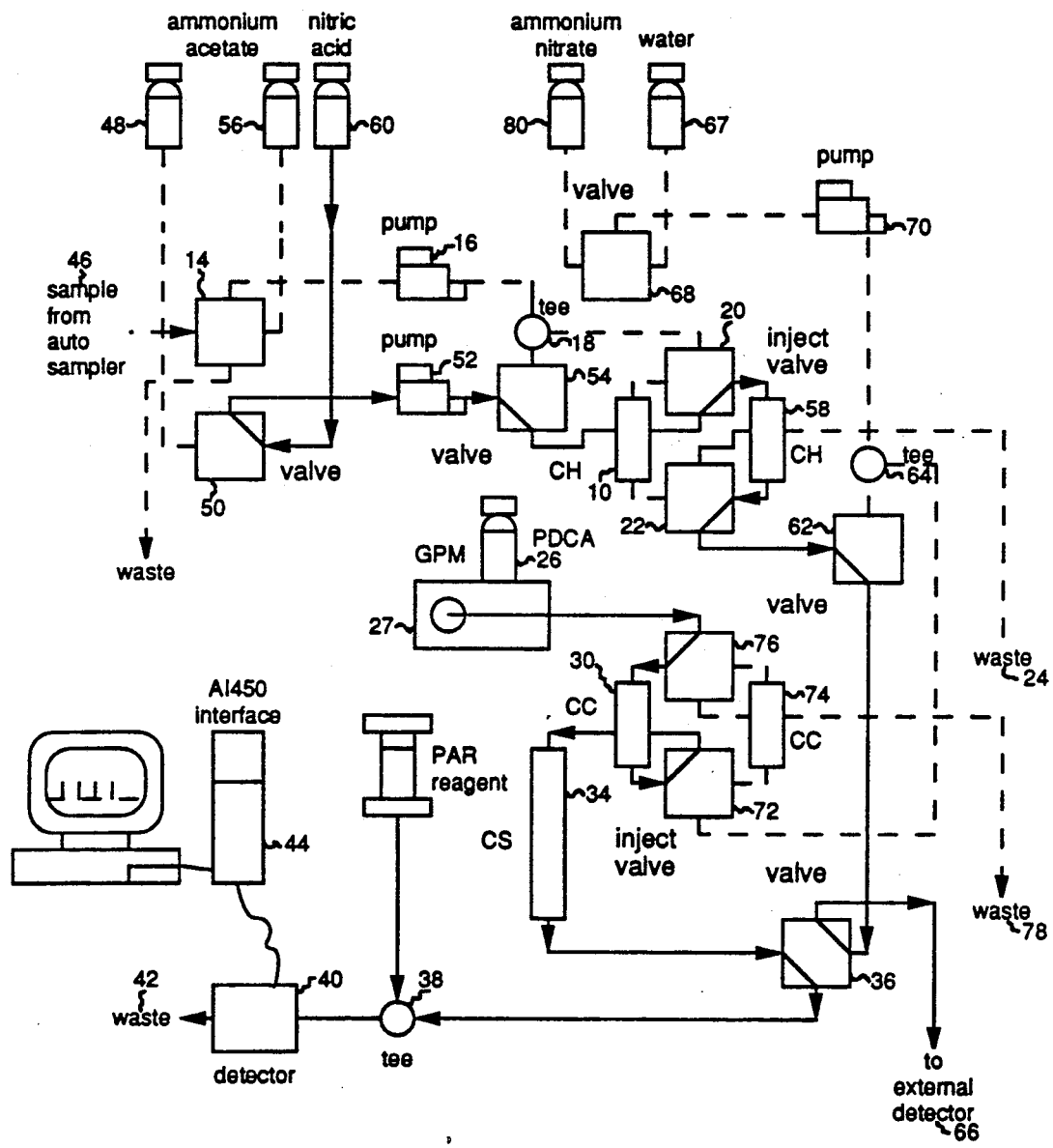

Referring to FIG. 6, the system is illustrated for a sample previously loaded on the second chelator column 58 from a previous run. Transition elements from chelator column 58 are removed by passing a strong acid (1.0 M nitric acid) from pressurized container 60 through valve 50, pump 52, (set at 1 ml/min) valve 54, valve 20 and into chelator column 58 through valve 22, valve 62 and 64 to waste or an external detector 66. During this time, analysis of transitional elements from concentrator column 10 is continuing.

Figure 7:
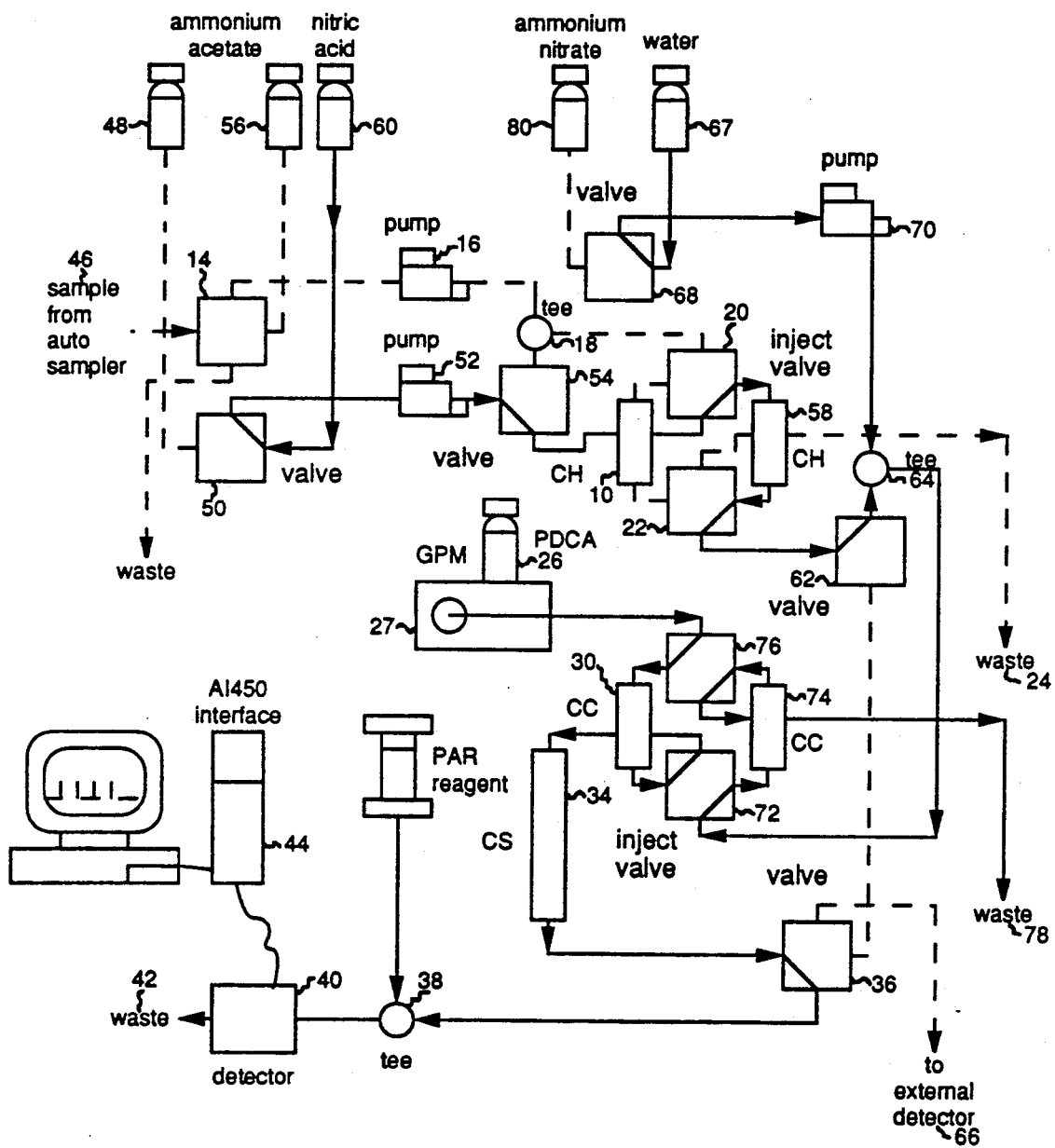

Referring to FIG. 7, the system is illustrated with sample previously loaded on concentrator column 58 from a previous run. Transition elements are removed from the chelator column by nitric acid from pressurized container 60 which passes by the route set forth in FIG. 6 through the column and valve 22 and 62 to mixing tee 64 where it is diluted with water from source 67, valve 68, pump 70 (set at 2 ml/min) and passes through valve 72 to concentrator column 74 where the transition elements are retained. From there the remainder of the effluent passes through valve 76 and to waste 78. During this time, analysis of the transition elements from concentrator column 30 is continuing.

Figure 8:
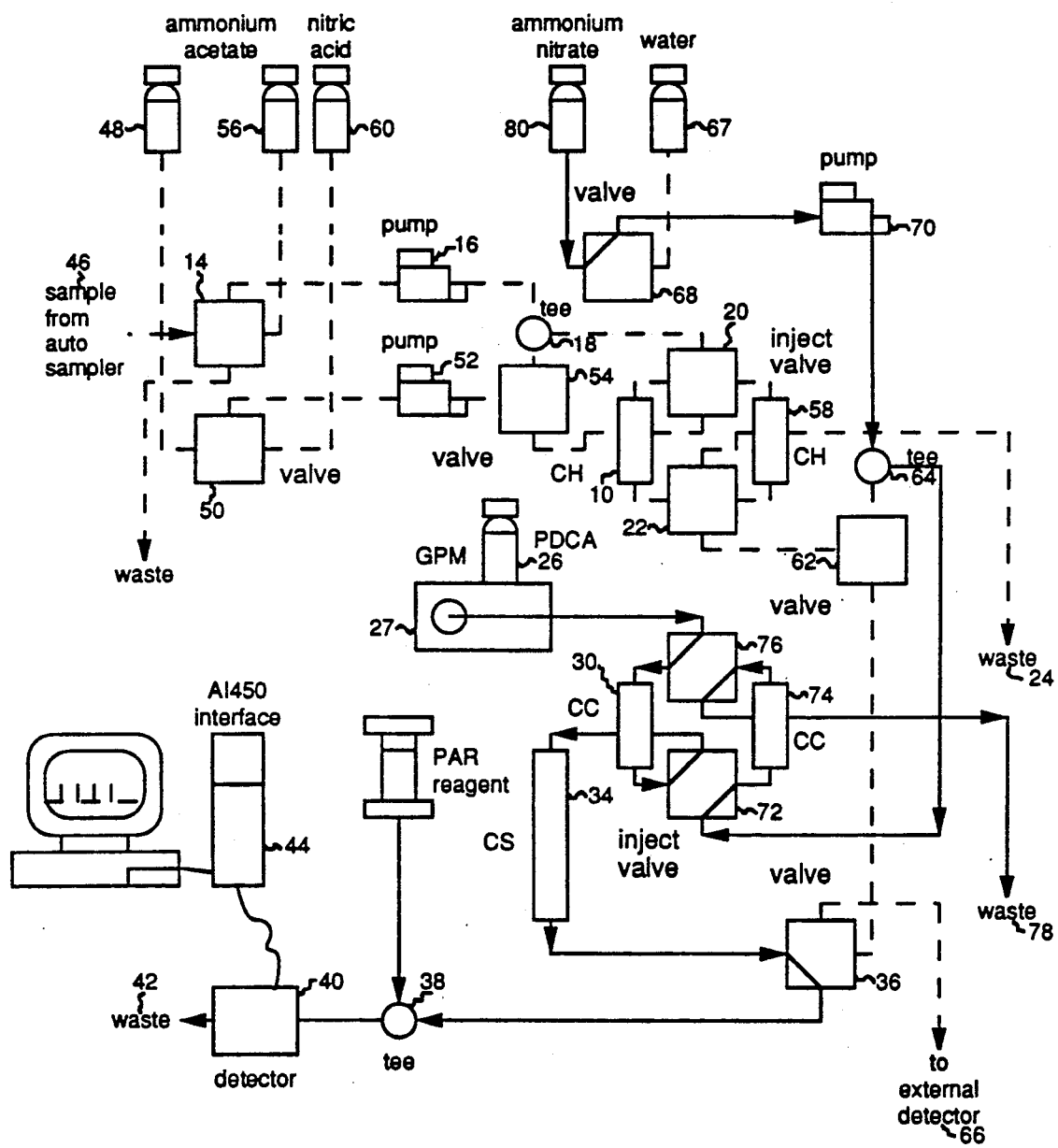

Referring to FIG. 8, the system is illustrated at a stage in which all transition elements are completely removed from chelator column 58 to concentrator column 74 with nitric acid eluant. At this time, concentrator column 74 is converted from hydrogen ion form to ammonium form by passing through it an ammonium salt, specifically 0.1 M ammonium nitrate (pH 3.5) solution. As illustrated in FIG. 8, this is accomplished by passing ammonium nitrate source in the form of pressurize container 80 through valve 68, pump 70, (set at 2 ml/min) mixing tee 64, concentrator column 74 and to waste 78. During this time, analysis of the transition elements from concentrator column 30 is continuing.

Figure 9:
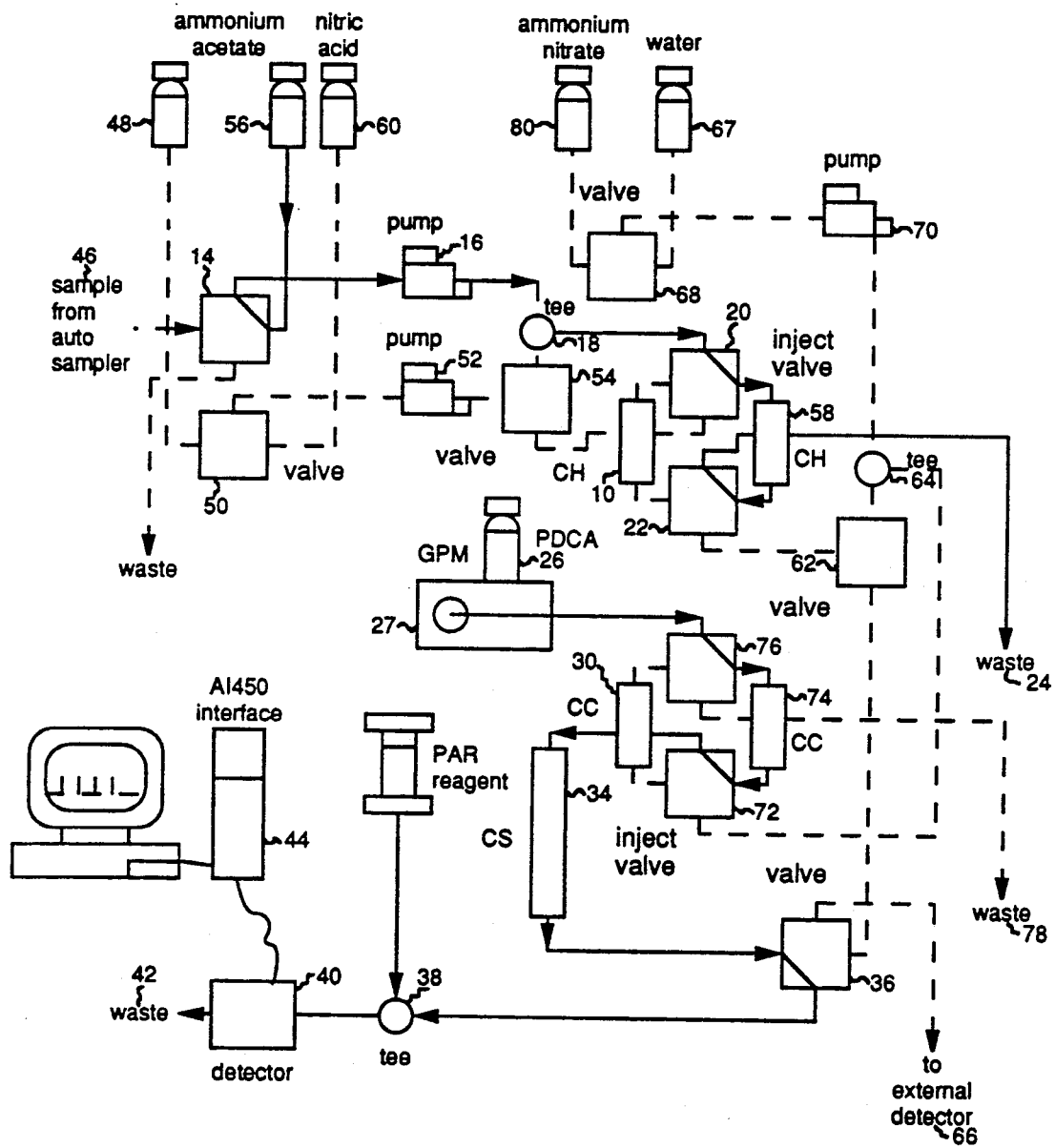

Referring to FIG. 9, chelator column 58 is buffered with 2 M ammonium acetate. Specifically, ammonium acetate from source 56 passes through valve 14, pump 16 (set at 2 ml/min), mixing tee 18, valve 20 through chelator column 58, valve 22 and to waste 24. If transition elements had been concentrated on concentrator column 74, metal analysis of transition elements and rare earth elements from that column commences at this time.

Figure 10:
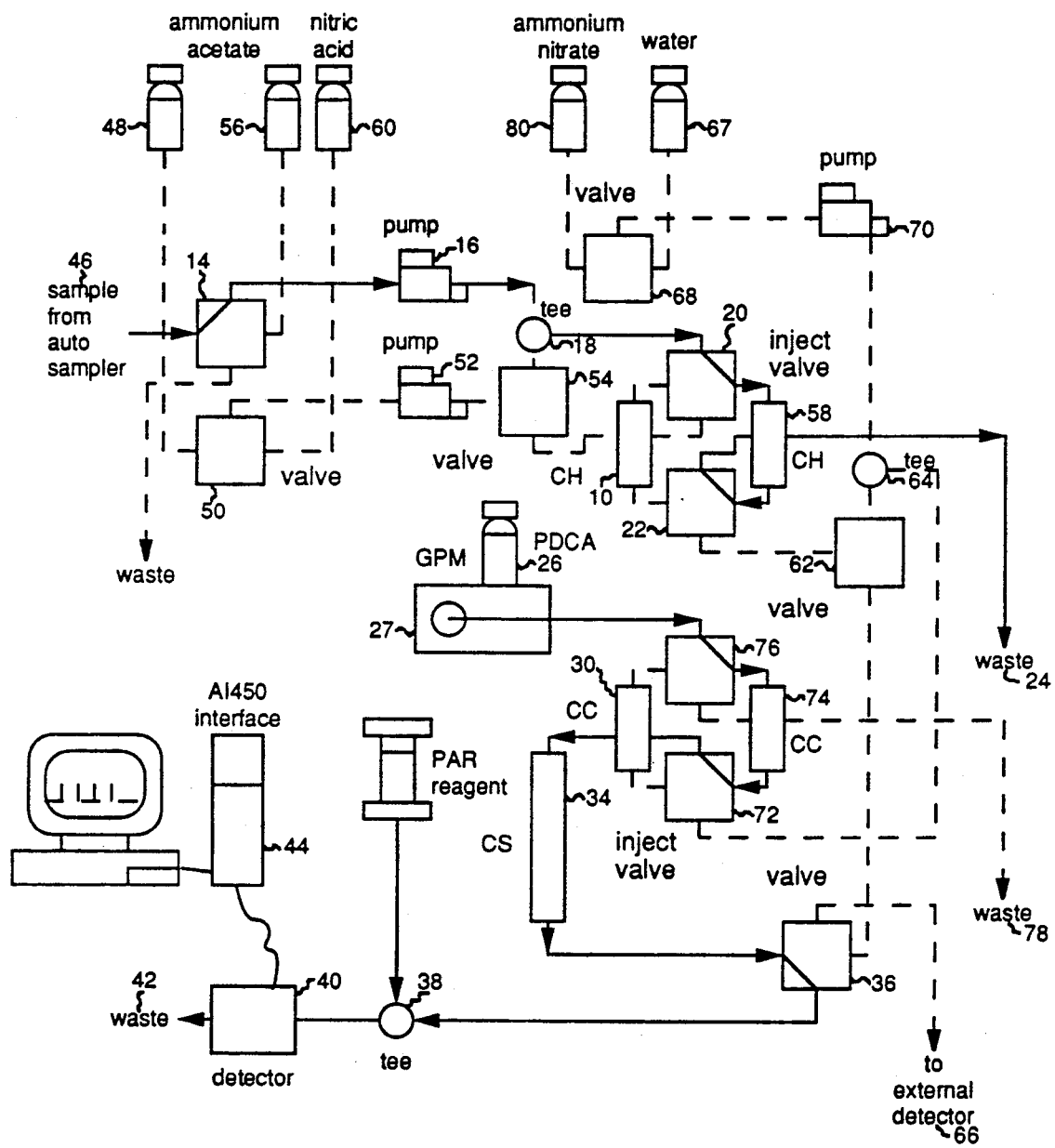

Referring to FIG. 10, sample from the auto sampler 46 is loaded onto chelator column 58 (at a flow rate of 2.0 mL/min and a sample pH of 5.2 to 5.5). Sample passes through valve 14, pump 16, mixing tee 18, valve 20, chelator column 58. The sample portion not retained passes to waste 24. During this time, analysis of transition elements from the concentrator column 74 is proceeding.

Figure 11:
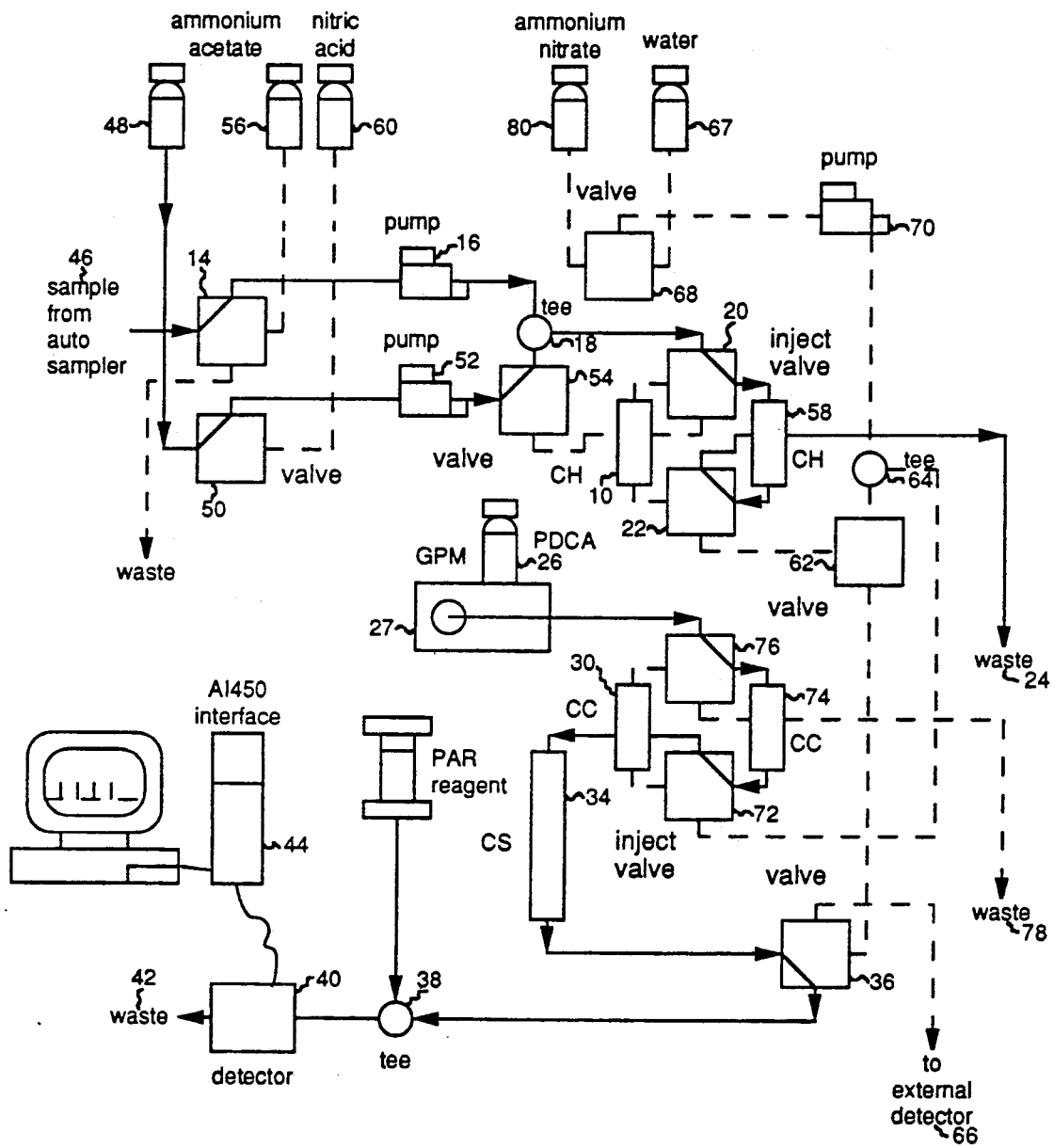

Referring to FIG. 11, an alternate loading procedure is illustrated for the same purpose is illustrated as described with respect to FIG. 4. A sample from autosampler 46 passes through valve 14, pump 16, mixing tee 18, valve 20, chelator 58, valve 22 and to waste. The ammonium acetate from source 48 passes through valve 56, pump 52, valve 50 and mixes in mixing tee 18 with sample, passes through valve 20, chelator column 58 and to waste 24. At this time, analysis of transition element from concentrator column 74 is continuing.

Figure 12:
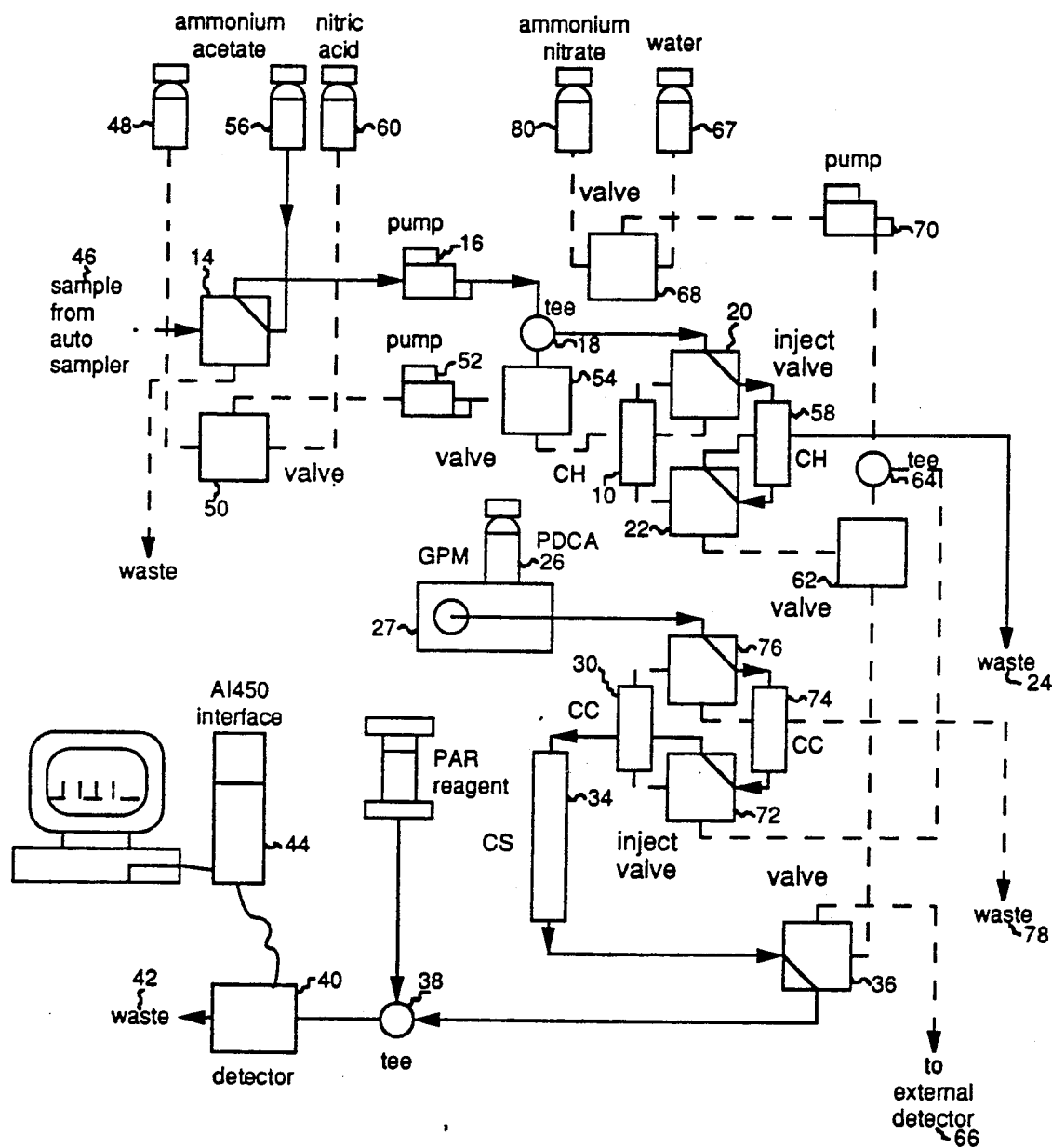

Referring to FIG. 12, alkali and alkaline earth metals are removed from chelator column 58 with 2 M ammonium acetate. Specifically, ammonium acetate from pressurized container 56 passes through valve 14, pump 16 (set at 2 mL/min), mixing tee 18, valve 20 through chelator column 58 and to waste 24. Transition element analysis from concentrator 74 continues.

Referring to FIG. 13, the system is illustrated using an external detector to analyze the transition elements removed from chelator column 10. Specifically, nitric acid from container 60 passes through valve 50, pump 52, valves 54 and 20, chelator column 10, valves 22, 62 and 36 to strip the transition elements and pass them to the external detector 66. Analysis from concentrator column is still in progress.

Figure 14:
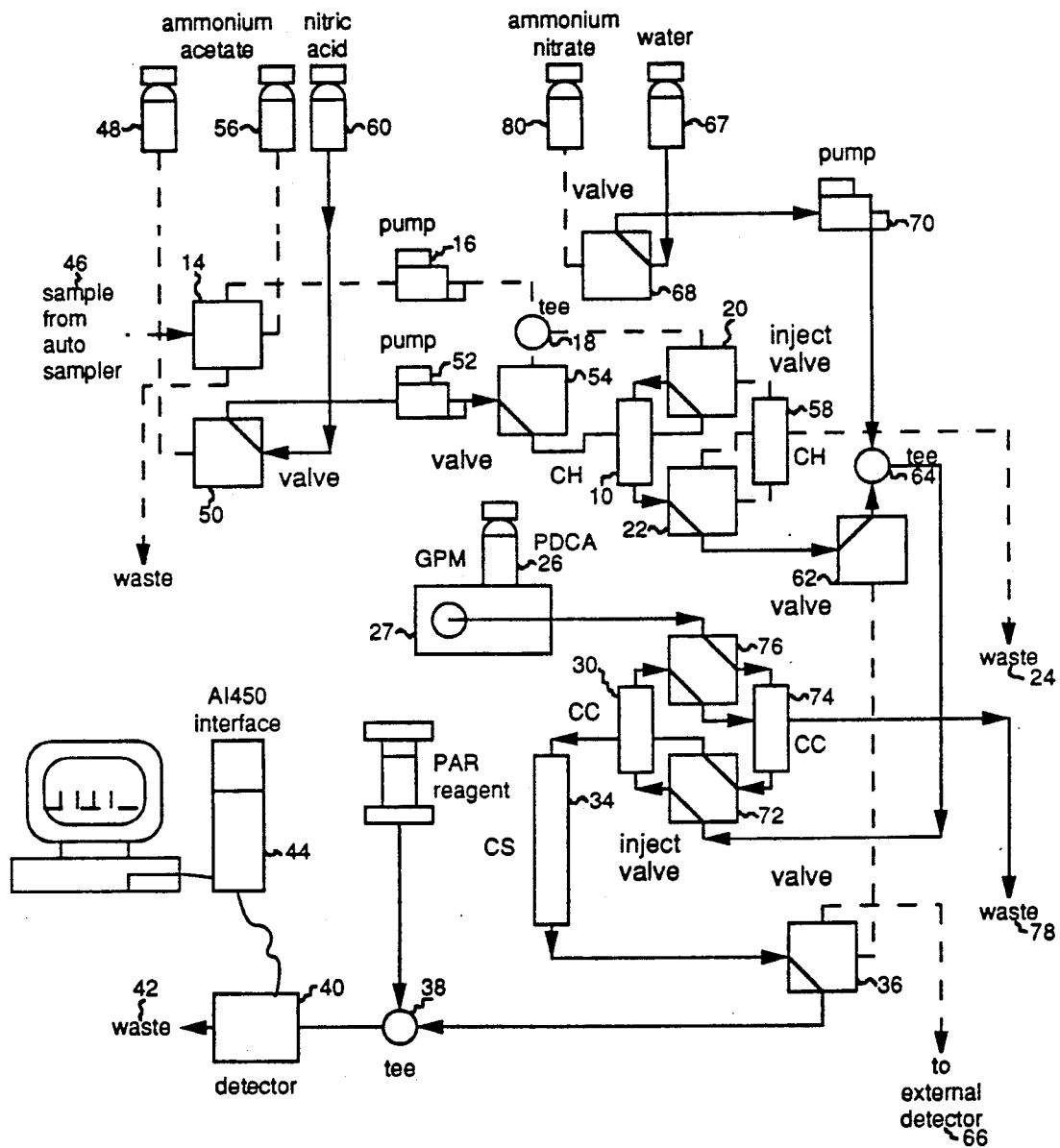

Referring to FIG. 14, sample previously had been loaded onto chelator column 10 from the previous run. Alkali and alkaline earth metal ions from the column are removed with 1 M nitric acid and diluted with water before the acid stream reaches concentrator column 30. Specifically, nitric acid from source 60 passes through valve 50, pump 52, valves 54 and 20 through chelator column 10, valves 22 and 62 and reaches mixing tee 64. At the same time, water from container 67 passes through valve 68, pump 70 and is mixed in mixing tee 64 with the effluent from chelator column 10. From there, chelator effluent passes through valve 72, concentrator column 30, valve 76 and to waste 78. During this stage, transition elements are being concentrated on concentrator column 30. Also, transition element analysis from concentrator column 74 is continuing.

Figure 15:
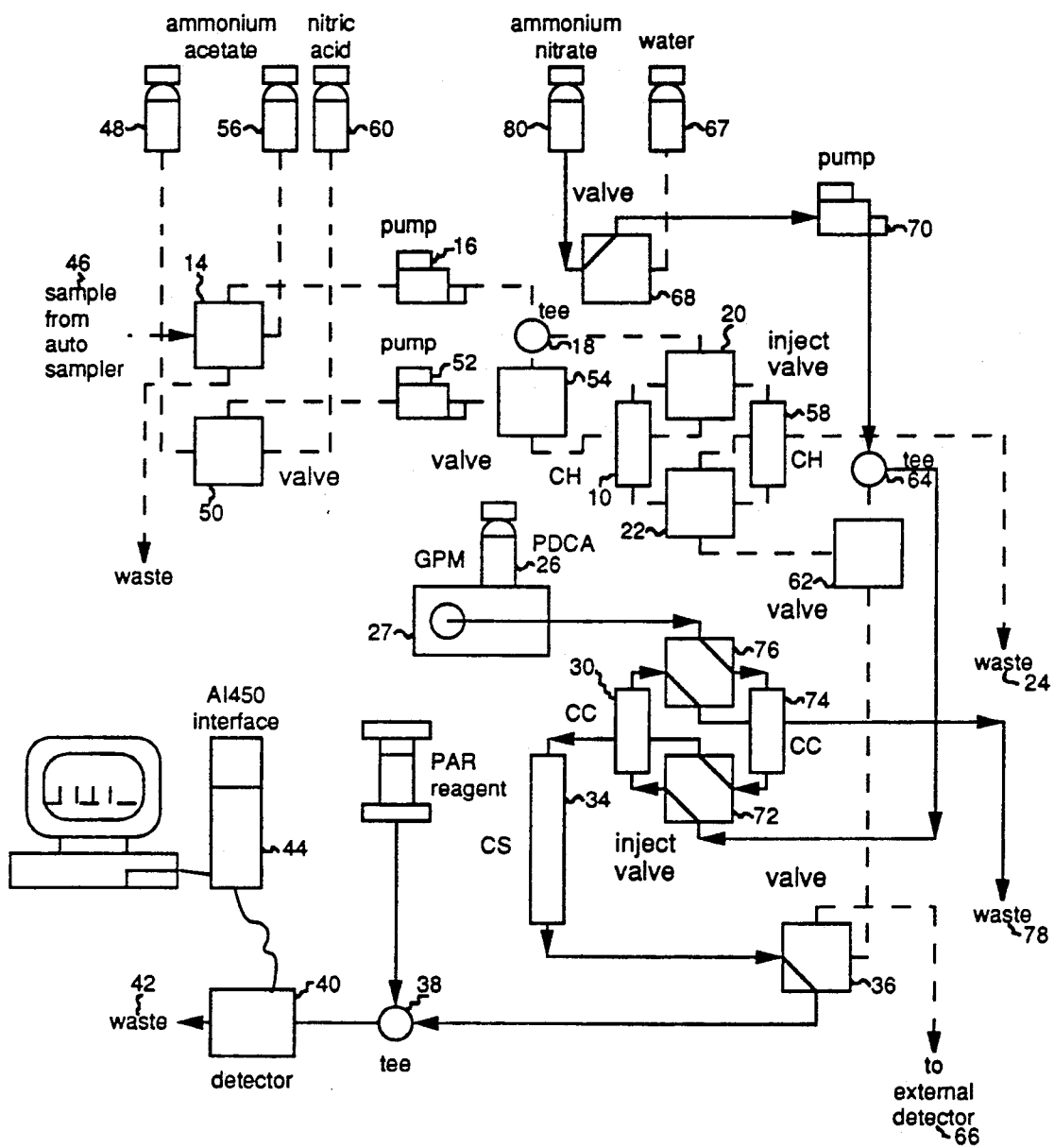

Referring to FIG. 15, after transition element ions are completely removed from chelator column 10 to concentrator column 30 with nitric acid, concentrator column 10 is converted from the hydrogen form to the ammonium form with 0.1 M ammonium nitrate solution (pH 3.5). Specifically, ammonium nitrate from container 80 passes through valve 68, pump 70, mixing tee 64, valve 72 through concentrator column 30 and to waste 78. Metal analysis from concentrator column 74 is continuing at this time.

Preferred conditions for the above system for some samples are as follows: (1) the chelator column is buffered with 5 ml of 2 M ammonium acetate, pH 5.5, (2) the sample or the standard is loaded onto the chelator column, (3) 12 ml of 2 M ammonium acetate is pumped through the column to remove Ca and Mg, (4) the concentrated transition and rare earth elements are removed with 5 ml of 1.0 M nitric acid and the acid effluent is diluted on-line with high purity water at the ratio of 1:2 (acid:water) to the concentrator column, (5) 6 mL of 0.1 M ammonium nitrate (pH 3.5) is pumped through the concentrator column to remove the hydronium ion, and finally, (6) transition and rare earth elements are eluted with PDCA eluate to the analytical column where the metal separation takes place.

The fully automated system is configured in such a way that it can perform simultaneous steps on two sets of the chelator and concentrator columns. This configuration permits a new sample to be determined every 20 minutes. The system is also configured to handle large sample volumes and functions as an autosampler capable of handling six different samples. All components in the system and data manipulation are controlled by AI400 program (Dionex Corp.)

The specific components used in the above Example 1 are as follows:
(1) chelation column—0.6 ml of macroporous iminodiacetate chelating resin (Duolite E5466 sold by Rohm & Haas) sized to 100μ.
(2) concentrator column high capacity cation exchange resin (sulfonate form of polystyrene-DVB, particle size of −400 mesh) Dowex 50,
(3) chromatographic column—supplied by Dionex Corporation (Ion pac CS5),
(4) Detector—UV vis absorbance 520 nm (Dionex VPM).

Examples 2-6 use the procedure of Example 1.

EXAMPLE 2

System Blank

Figure 16:
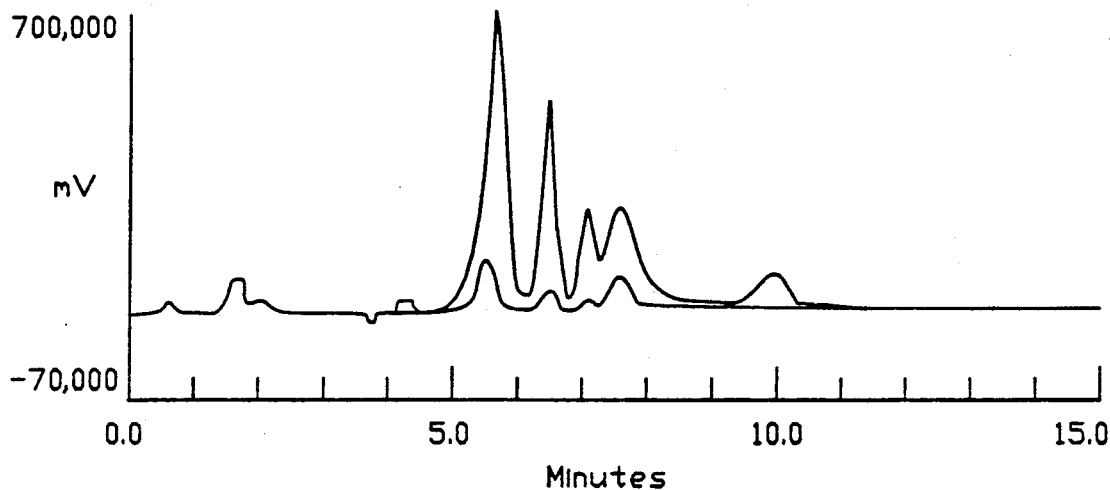

The system blank was determined by repeatedly running the analytical procedure as applied to the real sample. The main elements found in the system were Fe, Cu, Ni and Zn. Apparently, there are trace amounts of Fe and Zn which are slowly extracted from the chromatographic system. The levels of these extracted elements decreases with time. The lowest blank levels observed for the method, are about 10 ng of Fe, 15 ng for Zn and 2 ng for Cu and Ni. A typical system blank is shown in FIG. 16 as compared to transition metal levels detected in sea water.

EXAMPLE 3

Spiked Sea Water

Figure 17:
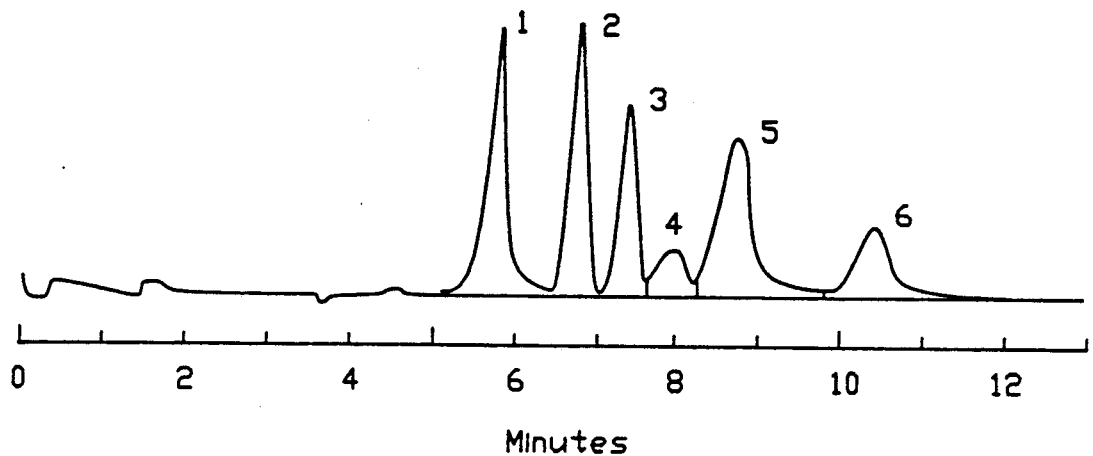

Sea water sample was spiked with six transition elements (Fe, Cu, Ni, Zn, Co and Mn) in sub ng levels. Typically, the sea water contains only small amounts of Co and, in order to detect it, more sea water was concentrated on the chelator column. FIG. 17 shows the spiked transition metals analyzed by the present system.

EXAMPLE 4

Sea Water

Figure 18:
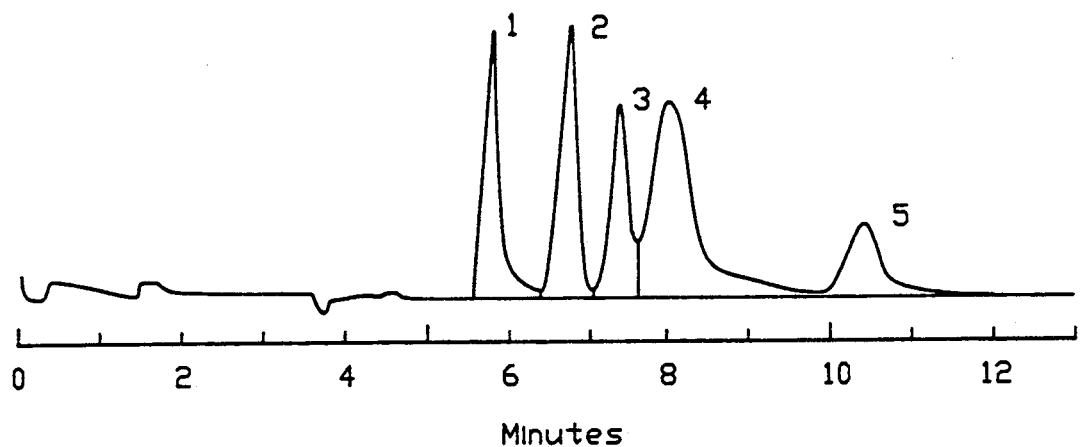

The first matrix which the method was applied to was sea water. A sea water was filtered and acidified to stabilize the free transition elements at the time of sample collection. (in a comparative experiment, the sea water sample was analyzed by Neutron Activation Analysis (NAA). The sample pH was adjusted to pH 5.5, the sample (20-200 mL) was concentrated on the chelator column and analyzed. FIG. 18 shows a typical chromatogram with levels as compared to the result obtained from NAA technique.

Figure 19:
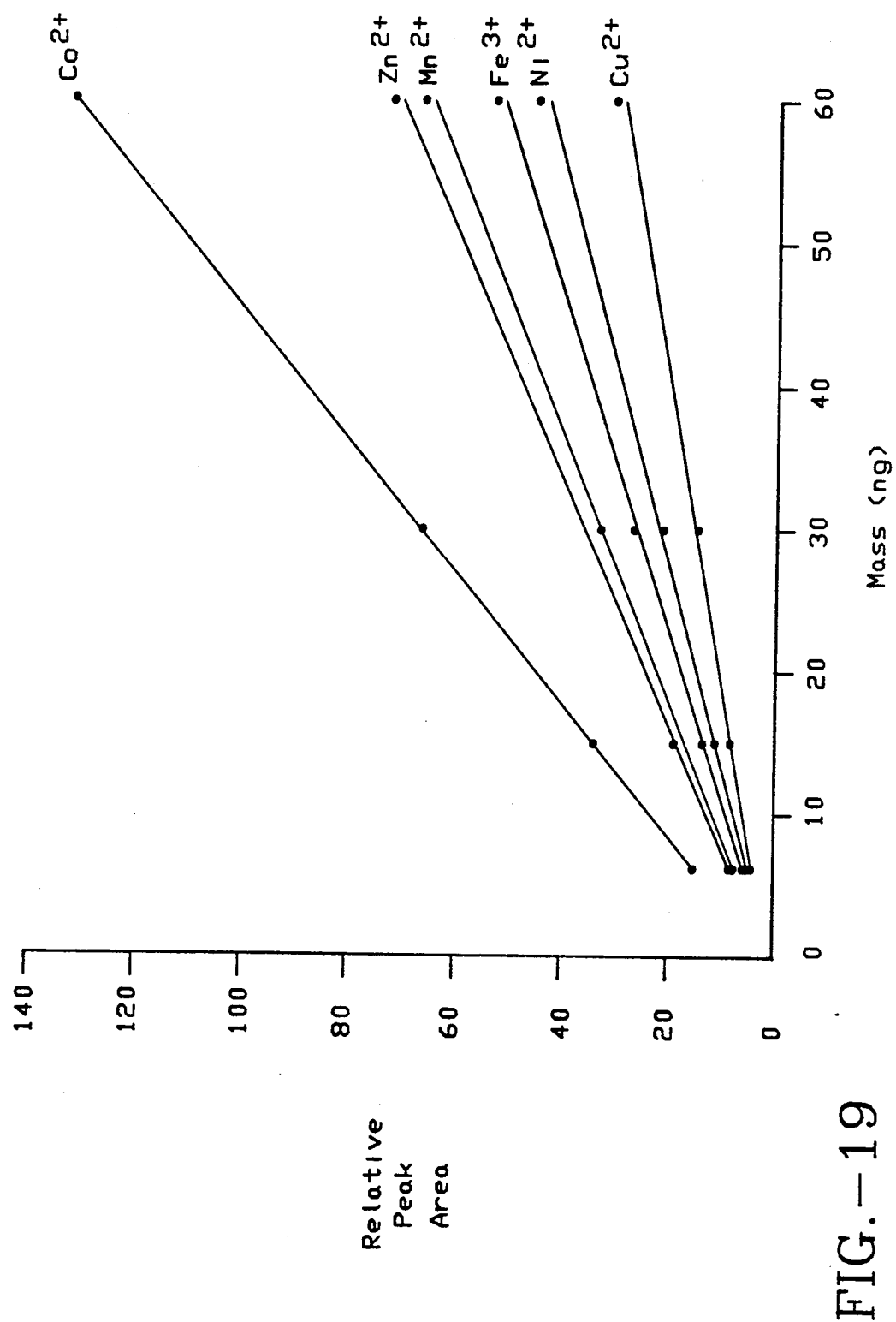

Linearity was studied in terms of both analyte concentration as well as sample volume. Sample as large as 200 mL were concentrated with good linearity. Also the sea water was spiked with metals to determine linearity. The sea water matrix linear range was evaluated from 0.5 ng (detection limit) to at least 60 ng for the metal studied in FIG. 19.

EXAMPLE 5

Oyster Tissue (SRM 1566)

Figure 20:
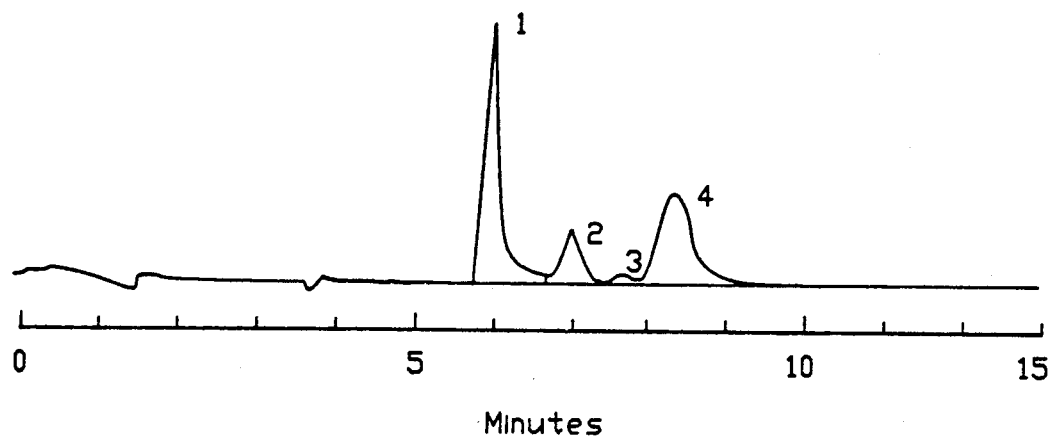

The next matrix which the method was applied to was acid digested oyster tissue Standard Reference Material (SRM 1566). A quarter gram sample was acid digested and the sample in approximately 10 mL acid solution was neutralized, buffered and diluted to 1000 mL with water. Five to 10 mL of the diluted sample was concentrated on the chelator column. FIG. 20 shows the analysis compared to certified values.

EXAMPLE 6

Bovine Liver

Another example was bovine liver (Standard Reference Material 1577a). A quarter gram sample of bovine liver was acid digested and approximately 10 mL of the sample was neutralized and buffered (pH 5.5), then diluted to 100 mL with water. Five to 10 mL of the diluted sample was concentrated on the chelator column. FIG. 21 shows a typical chromatogram of bovine liver with concentrations compared to certified results.

EXAMPLE 7

In this example, the procedure of example 1 was followed with a different highly selective chelating resin capable of separating the transition elements from the alkali and alkaline earth metals without a wash step.

A chelating column containing 1.7 ml of 300-100 μ resin was prepared using the XE-305, 8-hydroxyquinoline bonded resin from Seastar Instruments. The column was rinsed with 0.2 M HCl to remove any metal contamination on the resin. The column was then equilibrated with 8 ml of 2 M ammonium chloride, pH 10. (This chelating column is used in the same chromatographic system as the iminodiacetate column.) A 20 ml (sodium phosphate) buffered seawater sample (pH 7) was passed through the chelating column at a flow rate of 1.0 ml/min. The transition and lanthanides metals are concentrated but alkali and alkaline earth metals are not retained. Next, 3 ml of deionized water is passed through the column to elute the residual seawater present in the column void volume. Next, the chelating column is switched in line with the cation concentrator and 2.5 ml of 0.5 M nitric acid is used to elute the concentrated metals from the chelating column to the cation concentrator. The cation concentrator is next converted from the acid form to the ammonium form as in the iminodiacetate example. Finally, the cation concentrator is switched in-line with the analytical column and the transition metals are eluted to the analytical column by the PDCA eluant. The resulting chromatogram is identical to the iminodiacetate example. The XE-305, 8-hydroxyquinoline column is then regenerated with 8 ml of 2 M ammonium chloride, pH 10 and is ready for the next sample.

EXAMPLE 8

In this example, the method of Example 1 was followed except iron was retained on the concentrator column when the remainder of the transition elements were analyzed.

For the selective elution of iron, concentration on the chelator column is accomplished using the iminodiacetate chemistry of Example 1. 10 ml of a sample containing iron at the 100 ppm and other transition elements at 1 ppm are concentrated using the iminodiacetate concentrator. Once the alkali and alkaline earth metals have been eluted, a 0.1 M oxalic acid and 0.2 M ammonium hydroxide eluant is used to elute the transition elements from the chelating column to a column containing 2 ml of Dowex 2, 4% metals, except iron, are eluted with a volume of 5-10 ml from the anion concentrator, while the iron is strongly bound by the anion concentrator and not eluted. The effluent from the anion concentrator, containing the transition metals except iron, is then directed to a simultaneous inductively coupled plasma atomic emission spectrometer for detection. (Other detectors such as a sequential ICP or atomic absorption instrument can be used.) The concentrated iron is eluted form the anion concentrator using 20 ml of 0.2 M HCl. (Alternatively a cation concentrator can be used.)

EXAMPLE 9

Here, the concentrator column is the cation exchanger of Example 1. Using the oxalate eluant and sample mentioned above, the concentrated iron from the chelator elutes in the first 2 ml of the oxalate eluant, while the other transition elements would have an elution volume of 5-10 ml. Specifically, this example is for the detection of transition metals from sea water with selective elution of iron followed by ICP detection.

System:

Chelator—1.7 ml macroporous iminodiacetate chelating resin, 50-100 micron.

Concentrator—0.17 ml high capacity cation exchange resin, Dowex 50, 8% cross-linked, 50-100 micron.

Chromatographic system—Dionex 4000i IC.

Detector—Thermo Jarrell Ash ICAP61 spectrometer.

Conditions—10 ml of sea water sample spiked with 100 ppm iron and 1 ppm of copper, nickel, cobalt and zinc buffered to pH 5.5 with 2 M ammonium acetate, pH 5.5. Sample concentrated at 2.0 ml/min through chelator column. Next, 12 ml of 2 M ammonium acetate, pH 5.5 at 2.0 ml/min used to eluted alkali and alkaline earth metals form the chelator. Next, 15 ml of 0.1 M oxalic acid, 0.2 M ammonium hydroxide pumped through the chelator and to the cation concentrator finally to the ICP nebulizer where iron is detected in the first two ml and the other transition metals detected in the 5-10 ml band.

EXAMPLE 10

In this example the procedure of Example 1 is followed with a gradient eluate/PDCA buffer for the Ion Chromatograph. The system elutes the transition elements in a separate group from the lanthanide elements. The analytes are transition elements ($Fe^{3+}$, $Cu^{2+}$, $Ni^{2+}$, $Zn^{2+}$, $Co^{2+}$, $Mn^{2+}$, $Fe^{2+}$) and the lanthanide elements ($La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$).

| CONDITIONS | |
|---|---|
| Sample Loop Volume: | 50 μL |
| Separator Column: | HPIC-CS5 |
| Eluant 1: | DI Water |
| Eluant 2: | 6 mM PDCA |
| | 50 mM $CH_3CO_2Na$, |
| | 50 mM $CH_3CO_2H$ |
| Eluant 3: | 100 mM Oxalic Acid |
| Eluant 4: | 190 mM LiOH |
| | 100 mM Diglycolic Acid |
| | 190 mM LiOH |
| Flow Rate: | 1 ml/min. |
| Postcolumn Reagent: | 0.2 mM PAR, |
| | 3 M $NH_4OH$, |
| | 1 M $CH_3CO_2H$ |
| Reagent Flow Rate: | 0.7 ml/min. |
| Mixing Device: | Membrane Reactor, |
| | Reaction Coil |
| Detector Wavelength: | 520 nm |

| Gradient Program for GPM: | | | | |
|---|---|---|---|---|
| Time | Eluant 1 | Eluant 2 | Eluant 3 | Eluant 4 |
| 0.0 | 0 | 100 | 0 | 0 |
| 12.0 | 0 | 100 | 0 | 0 |
| 12.1 | 100 | 0 | 0 | 0 |
| 17.0 | 100 | 0 | 0 | 0 |
| 17.1 | 40 | 0 | 60 | 0 |
| 21.0 | 40 | 0 | 60 | 0 |
| 21.1 | 20 | 0 | 80 | 0 |
| 30.0 | 51 | 0 | 26 | 23 |

Reset the GPM to time zero conditions after the analysis had completed. Hold at initial conditions for 10 minutes before the next injection is made.

| SOLUTIONS AND REAGENTS | |
|---|---|
| Eluant 2: | 6 mM PDCA, |
| | 50 mM $CH_3CO_2Na$, |
| | 50 mM $CH_3CO_2H$ |

Prepare by dissolving the following reagents, in the order listed, in 18 M-ohm deionized water:
    50.0 mM (6.8 g/L) sodium acetate, trihydrate
    6.0 mM (1.0 g/L) pyridine-2, 6-dicarboxylic acid (PDCA)
    50.0 mM (2.85 mL/L) glacial acetic acid
The PDCA is slow to dissolve and may require stirring.

| Eluant 3: | 100 mM Oxalic Acid, |
|---|---|
| | 190 mM LiOH |

Prepared by dissolving the following reagents in 18 M-ohm deionized water:
    100 mM (12.61 g/L) oxalic acid, dihydrate
    190 mM (4.55 g/L) lithium hydroxide

| Eluant 4: | 100 mM Diglycolic Acid, |
|---|---|
| | 190 mM LiOH |

Prepared by dissolving the following reagents in 18 M-ohm deionized water:
    100 mM (13.41 g/L) diglycolic acid
    190 mM (4.55 g/L) lithium hydroxide

| Postcolumn Reagent: | 0.2 mM PAR, |
|---|---|
| | 3 M $NH_4OH$ |
| | 1 M $CH_3CO_2H$ |

Add 200 ml of 30% trace metal grade ammonium hydroxide to about 400 ml of 18 M-ohm deionized water in a 1 L container. Add and dissolve 0.05 g of PAR. Add 57 Ml of trace metal grade glacial acetic acid, mix, and dilute to 1 L.

EXAMPLE 11

This example illustrates analysis of transition elements isolated from iron as in Example 8.

ANALYTES

Divalent cations of lead, copper, cadmium, manganese, cobalt, zinc and nickel.

Transition metals are separated as both cationic and anionic complexes with the oxalate chelating agent added to the eluant. Using this method, cadmium and manganese coelute.

The metals are detected by measuring the absorbance at 520 nm of the complex formed with the postcolumn PAR reagent. The prepared PAR reagent is also easily oxidized.

| CONDITIONS | |
|---|---|
| Single Loop Volume: | 50 μL |
| Separator Column: | HPIC-CS5 |
| Eluant: | 50 mM Oxalic Acid, |
|  | 95 mM Lithium Hydroxide |
| Flow Rate: | 1.0 mL/min. |
| Mixing Device: | Membrane Reactor |
| Postcolumn Reagent: | 0.3 mM PAR, |
|  | 1 M Acetic Acid, |
|  | 3 M ammonium Hydroxide |
| Reagent Flow Rate: | 0.7 mL/min. |
| Detector Wavelength: | 520 nm |
| SOLUTION AND REAGENTS | |
| Eluant: | 50 mM Oxalic Acid |
|  | 95 mM Lithium Hydroxide |

Dissolve 6.3 g of oxalic acid dihydrate and 4.0 g lithium hydroxide monohydrate per liter of water. The eluant pH should be 4.8.

| Postcolumn Reagent: | 0.3 mM PAR, |
|---|---|
|  | 1 M Acetic Acid, |
|  | 3 M Ammonium Hydroxide |

Place 400 mL of water in a 1 L container. Add 200 ml of trace metal grade 30% ammonium hydroxide solution. Add and dissolve 0.077 g PAR [4-(2-pyridylazo)-resorcinol]. Add 57 ml trace metal grade glacial acetic acid. Fill with water to 1 L.

The foregoing examples illustrate two completes cycles through the system of two samples through two pairs of chelating and concentrator columns.

For certain applications, the system may be used with a different form of detector without the need for chromatography. This forms part of the present invention. Further, as described above, in some instances, where the chelator resin has sufficient specificity, it may retain the transition elements and rare earth elements while passing the alkali metals and alkaline earth metals. This would eliminate a step in the procedure and would correspondently simplify the valving required.

Also, the chelator means and concentrator means have been described in the form of resin column. However, charged membrane systems, e.g. of the membrane suppressor type sold by Dionex Corporation could be substituted.

What is claimed is:

1. A method for the detection of selected trace transition elements, rare earth elements, or both, in an aqueous sample including the same, together with alkali metals, alkaline earth elements, or both, said method comprising
   (a) flowing said sample through chelator means, comprising ion exchange means having functional groups, under conditions for retaining substantially all of said transition elements and rare earth elements in said sample but for retaining only part of said alkali metals and alkaline earth metals in said sample,
   (b) flowing a first eluant through said chelator means capable of stripping and removing in a waste stream said retained alkali metals and alkaline earth metals, but not transition elements and rare earth elements from said chelator means,
   (c) flowing a second eluant through said chelator means to strip said retained transition elements and rare earth elements therefrom and form a chelator effluent stream,
   (d) flowing said chelator effluent stream from step (c) through a concentrator means, comprising ion exchange resin means, to retain said transition elements and rare earth elements therein while passing the remainder of said chelator effluent stream,
   (e) discontinuing the flow of said chelator effluent stream to said concentrator means,
   (f) passing a third eluant, comprising an aqueous solution of a chelator complex agent, through said concentrator means, under conditions to elute at least selected ones of said transition elements and rare earth elements in chelated complexes in a concentrator effluent stream, and
   (g) passing said concentrator effluent stream to a detector in which said selected transition elements and rare earth elements are detected.

2. The method of claim 1 further comprising, prior to step (g), the step of passing said concentrator effluent stream through separator means in which said transition elements and rare earth elements are separated on elution in a separator effluent stream wherein said separator effluent stream is passed to said detector.

3. The method of claim 2 in which said separator means comprises chromatographic separation means.

4. The method of claim 2 in which said concentrator effluent stream includes essentially no metal other than the selected transition and rare earth eluants in the sample.

5. The method of claim 1 in which said concentrator means is in cationic form during step (f).

6. The method of claim 1 in which, during step (f), said concentrator means is in a cationic form other than hydronium to facilitate formation of said chelated complexes.

7. The method of claim 6 in which said concentrator means is in hydronium form after step (c) and is converted to another cationic form by equalibrating said concentrator means with a cationic salt formed of a cation and anion.

8. The method of claim 7 in which the cation of said cationic salt is selected from the group consisting of ammonium and alkali metal salts.

9. The method of claim 8 in which the cation of said cationic salt comprises ammonium ion.

10. The method of claim 9 in which said cationic salt comprises ammonium nitrate.

11. The method of claim 1 in which, in step (d), at least one of the said transition elements or rare earth elements in said chelator effluent stream passes through said concentrator means without being retained therein.

12. The method of claim 1 in which at least one of said transition elements or rare earth elements retained on said concentrator means in step (d) is not eluted in said concentrator effluent stream in step (f).

13. The method of claim 12 in which said ion exchange resin means in said concentrator means in step (d) is in anionic form, and in which said chelator complex agent is constructed so as to form an anionic complex with said selected transition elements and rare earth elements.

14. The method of claim 1 in which the functional groups of said ion exchange means are selected from the group consisting of thiols, amino acid chelators, carboxylates, and polyamines.

15. The method of claim 1 in which the functional groups of said ion exchange means are selected from the group consisting of iminodiacetate, 8-hydroxyquinoline, dithiocarbonate, amidoxime, and aminomethylphosphonic acid.

16. The method of claim 1 in which during step (a) the pH level in said chelator means during sample flow therethrough is from about 4.0 to about 9.0.

17. The method of claim 1 in which during step (c) the pH level in said chelator means during sample flow therethrough is less than about 1.

18. The method of claim 1 in which during step (f) the pH level in said concentrator means during passage of said third eluant therethrough is from about 4.0 to about 5.0.

19. The method of claim 1 in which said second eluant comprises a strongly acidic aqueous solution.

20. The method of claim 1 in which said chelate complex agent is selected from the group consisting of pyridine-2, 6-dicarboxylic acid, oxalic acid, tartaric acid, and citric acid.

21. A method for the detection of selected trace transition elements, rare earth elements, or both, in an aqueous sample including the same, together with alkali metals, alkaline earth elements, or both, said method comprising
   (a) flowing said sample through a chelator means, comprising chelator resin, under conditions for retaining substantially all of the transition elements and rare earth elements in said sample but not retaining alkali metals and alkaline earth metals in said sample,
   (b) flowing a first eluant through said chelator resin to strip said retained transition elements and rare earth elements therefrom and form a chelator effluent,
   (c) flowing the chelator effluent stream from step (b) through a concentrator means, comprising ion exchange resin, to retain said transition elements and rare earth elements while passing the remainder of said chelator effluent stream,
   (d) discontinuing the flow of said chelator effluent stream to said concentrator means,
   (e) passing a second eluant comprising an aqueous solution of a chelator complex agent, through said concentrator means, under conditions to elute at least selected ones of said transition elements and rare earth elements in chelated complexes in a concentrator effluent stream, and
   (f) passing said concentrator effluent stream to a detector in which said selected transition elements and rare earth elements are detected.

22. The method of claim 21 further comprising, prior to step (f), the step of passing said concentrator effluent stream through separator means in which said transition elements and rare earth elements are separated on elution in a separator effluent stream, wherein said separator effluent stream is passed to said detector means.

23. The method of claim 22 in which said separator means comprises chromatographic separation means.

24. A continuous method for the detection of selected transition elements or rare earth elements, or both, in an aqueous sample including the same, together with alkali metals or alkaline earth elements, or both, said method comprising
   (a) flowing said sample through chelating resin bed means, comprising function group, under controlled, pressurized non-gravity flow conditions and under conditions for chelating with and thereby retaining substantially all of the transition elements and rare earth elements in said sample, but for retaining only part of the alkali metals and alkaline earth metals in said sample,
   (b) flowing a first eluant under controlled, pressurized, non-gravity flow conditions through said chelator means capable of stripping and removing in a waste stream said retained alkali metals and alkaline earth metals, but not said transition elements and rare earth elements, from said chelator means,
   (c) flowing a second eluant under controlled, pressurized, non-gravity flow conditions through said chelating resin bed means to strip said retained transition elements and rare earth elements therefrom and form a chelator effluent stream, and
   (d) passing said chelator effluent stream in a pressurized continuous stream directly from said chelator means to an elemental detector in which individual ones of said selected transition elements and rare earth elements are detected.

25. The method of claim 24 in which the functional groups of said chelating resin bed means are selected from the group consisting of thiols, amino acid chelators, carboxylates, and polyamines.

26. The method of claim 24 in which the functional groups of said chelating resin bed means are selected from the group consisting of iminodiacetate, 8-hydroxyquinoline, dithiocarbonate, amidoxime, and aminomethylphosphonic acid.

27. A continuous method for the detection of selected transition elements or rare earth elements, or both, in an aqueous sample including the same, together with alkali metals or alkaline earth elements, or both, said method comprising
   (a) flowing said sample through chelating resin bed means under controlled pressurized non-gravity flow conditions and under conditions for chelating with and thereby retaining substantially all of the transition elements and rare earth elements in said sample but not retaining alkali metals and alkaline earth metals in said sample,
   (b) flowing an eluant through said chelating resin bed means under controlled, pressurized non-gravity flow conditions to strip said retained transition elements and rare earth elements therefrom and form a chelator effluent, and
   (c) passing said chelator effluent stream in a pressurized continuous stream directly from said chelator means to an elemental detector in which individuals ones of said selected transition elements and rare earth elements are detected.

* * * * *